(12) United States Patent
Allis et al.

(10) Patent No.: US 10,765,807 B2
(45) Date of Patent: Sep. 8, 2020

(54) FLUID DELIVERY DEVICE WITH SENSOR

(71) Applicant: Insulet Corporation, Acton, MA (US)

(72) Inventors: Daniel Allis, Boxford, MA (US);
Kenneth Phillips, Boston, MA (US);
Jacob Anthony Coumans, Old Lyme, CT (US)

(73) Assignee: INSULET CORPORATION, Acton, MA (US)

( * ) Notice: Subject to any disclaimer, the term of this patent is extended or adjusted under 35 U.S.C. 154(b) by 113 days.

(21) Appl. No.: 15/714,496

(22) Filed: Sep. 25, 2017

(65) Prior Publication Data

US 2018/0085521 A1    Mar. 29, 2018

Related U.S. Application Data

(60) Provisional application No. 62/398,792, filed on Sep. 23, 2016.

(51) Int. Cl.
*A61M 5/168*     (2006.01)
*A61M 5/142*     (2006.01)
(Continued)

(52) U.S. Cl.
CPC ...... *A61M 5/16854* (2013.01); *A61M 5/1452* (2013.01); *A61M 5/14248* (2013.01);
(Continued)

(58) Field of Classification Search
CPC ..... G06F 19/3468; A61M 2005/14264; A61M 2005/16863; A61M 2205/18;
(Continued)

(56) References Cited

U.S. PATENT DOCUMENTS 3,963,380 A * 6/1976 Thomas, Jr. ...... A61M 5/14276
417/413.2
4,151,845 A * 5/1979 Clemens ............. A61M 5/1723
128/DIG. 13
(Continued)

FOREIGN PATENT DOCUMENTS

| AU | 2015301146 A1 | 3/2017 |
|---|---|---|
| EP | 2943149 A1 | 11/2015 |
| EP | 3177344 A1 | 6/2017 |
| EP | 3314548 A1 | 5/2018 |
| WO | 2005113036 A1 | 12/2005 |
| WO | 2012177353 A1 | 12/2012 |

(Continued)

OTHER PUBLICATIONS

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
(Continued)

*Primary Examiner* — Jason E Flick
*Assistant Examiner* — Mark A Igel

(57) ABSTRACT

A wearable drug delivery device for monitoring unintended over-delivery and/or under-delivery of a stored liquid drug are provided. An absolute pressure sensor can be positioned within the fluid path of the drug delivery device. The absolute pressor sensor can detect both ambient pressure (e.g., absolute or atmospheric pressure) and relative pressure (gage or pumping pressure). Based on the detected pressures, the effects of external ambient pressure on air with the fluid path can be determined during both intended drug delivery events and unintended drug delivery events. In turn, under-delivery and/or over-delivery of the liquid drug can be determined. Based on the severity of the determined under-delivery or over-delivery of the liquid drug, alarms indicating different urgencies can be provided to the user.

25 Claims, 11 Drawing Sheets

(51) Int. Cl.
  *A61M 5/145* (2006.01)
  *G06F 19/00* (2018.01)
(52) U.S. Cl.
  CPC ..... *A61M 5/16831* (2013.01); *G06F 19/3468* (2013.01); *A61M 2005/14264* (2013.01); *A61M 2005/16863* (2013.01); *A61M 2205/18* (2013.01); *A61M 2205/3331* (2013.01); *A61M 2205/3334* (2013.01); *A61M 2205/3368* (2013.01); *A61M 2205/3379* (2013.01); *A61M 2205/581* (2013.01); *A61M 2205/582* (2013.01); *A61M 2205/583* (2013.01); *A61M 2205/70* (2013.01)
(58) Field of Classification Search
  CPC .......... A61M 5/16854; A61M 5/14248; A61M 5/1452; A61M 5/16831
  See application file for complete search history.

(56) References Cited

U.S. PATENT DOCUMENTS

| | | | |
|---|---|---|---|
| 4,373,527 A | 2/1983 | Fischell | |
| 4,469,481 A | 9/1984 | Kobayashi | |
| 4,475,901 A | 10/1984 | Kraegen et al. | |
| 4,529,401 A * | 7/1985 | Leslie | A61M 5/1456 |
| | | | 128/DIG. 1 |
| 4,559,037 A | 12/1985 | Franetzki et al. | |
| 4,624,661 A | 11/1986 | Arimond | |
| 4,685,903 A | 8/1987 | Cable et al. | |
| 4,731,726 A | 3/1988 | Allen, III | |
| 4,808,161 A | 2/1989 | Kamen | |
| 5,153,827 A * | 10/1992 | Coutre | A61M 5/16831 |
| | | | 604/111 |
| 5,232,439 A | 8/1993 | Campbell et al. | |
| 5,244,463 A | 9/1993 | Cordner, Jr. et al. | |
| 5,281,808 A | 1/1994 | Kunkel | |
| 5,342,298 A * | 8/1994 | Michaels | A61M 25/1018 |
| | | | 128/DIG. 1 |
| 5,389,078 A * | 2/1995 | Zalesky | A61M 5/14526 |
| | | | 604/151 |
| 5,411,889 A | 5/1995 | Hoots et al. | |
| 5,421,812 A * | 6/1995 | Langley | A61M 1/303 |
| | | | 604/6.07 |
| 5,468,727 A | 11/1995 | Phillips et al. | |
| 5,507,288 A | 4/1996 | Bocker et al. | |
| 5,533,389 A | 7/1996 | Kamen et al. | |
| 5,665,065 A | 9/1997 | Colman et al. | |
| 5,678,539 A | 10/1997 | Schubert et al. | |
| 5,685,844 A | 11/1997 | Marttila | |
| 5,935,099 A | 8/1999 | Peterson et al. | |
| 6,024,539 A | 2/2000 | Blomquist | |
| 6,477,901 B1 * | 11/2002 | Tadigadapa | G01F 1/8404 |
| | | | 73/861.352 |
| 6,544,212 B2 | 4/2003 | Galley et al. | |
| 6,554,798 B1 | 4/2003 | Mann et al. | |
| 7,018,360 B2 | 3/2006 | Flaherty et al. | |
| 7,651,845 B2 | 1/2010 | Doyle, III et al. | |
| 8,452,359 B2 | 5/2013 | Rebec et al. | |
| 8,454,576 B2 | 6/2013 | Mastrototaro et al. | |
| 8,467,980 B2 | 6/2013 | Campbell et al. | |
| 8,478,557 B2 | 7/2013 | Hayter et al. | |
| 8,547,239 B2 * | 10/2013 | Peatfield | A61M 5/1413 |
| | | | 340/603 |
| 8,597,274 B2 | 12/2013 | Sloan et al. | |
| 8,622,988 B2 | 1/2014 | Hayter | |
| 8,810,394 B2 * | 8/2014 | Kalpin | A61M 5/14276 |
| | | | 340/540 |
| 9,171,343 B1 | 10/2015 | Fischell et al. | |
| 9,579,456 B2 | 2/2017 | Budiman et al. | |
| 9,907,515 B2 | 3/2018 | Doyle, III et al. | |
| 9,984,773 B2 | 5/2018 | Gondhalekar et al. | |
| 10,248,839 B2 * | 4/2019 | Levy | G06K 9/00228 |
| 2001/0034023 A1 * | 10/2001 | Stanton, Jr. | C12Q 1/6883 |
| | | | 435/6.16 |
| 2001/0034502 A1 * | 10/2001 | Moberg | A61M 5/1456 |
| | | | 604/154 |
| 2002/0016568 A1 * | 2/2002 | Lebel | A61N 1/37211 |
| | | | 604/131 |
| 2002/0161288 A1 | 10/2002 | Shin et al. | |
| 2003/0060692 A1 | 3/2003 | Ruchti et al. | |
| 2003/0220605 A1 * | 11/2003 | Bowman, Jr. | A61M 1/28 |
| | | | 604/29 |
| 2004/0133166 A1 * | 7/2004 | Moberg | A61M 5/1456 |
| | | | 604/151 |
| 2004/0171983 A1 * | 9/2004 | Sparks | A61M 5/16827 |
| | | | 604/65 |
| 2005/0075624 A1 * | 4/2005 | Miesel | A61M 5/14276 |
| | | | 604/505 |
| 2005/0272640 A1 | 12/2005 | Doyle, III et al. | |
| 2005/0277912 A1 * | 12/2005 | John | G16H 20/17 |
| | | | 604/890.1 |
| 2006/0270983 A1 * | 11/2006 | Lord | A61M 5/14276 |
| | | | 604/131 |
| 2007/0249007 A1 * | 10/2007 | Rosero | A61B 5/14532 |
| | | | 435/14 |
| 2008/0033272 A1 | 2/2008 | Gough et al. | |
| 2008/0206067 A1 * | 8/2008 | De Corral | F04B 11/0058 |
| | | | 417/53 |
| 2008/0269714 A1 | 10/2008 | Mastrototaro et al. | |
| 2009/0069745 A1 | 3/2009 | Estes et al. | |
| 2009/0105573 A1 | 4/2009 | Malecha | |
| 2009/0156924 A1 | 6/2009 | Shariati et al. | |
| 2009/0163781 A1 | 6/2009 | Say et al. | |
| 2009/0198350 A1 | 8/2009 | Thiele | |
| 2010/0057042 A1 * | 3/2010 | Hayter | A61M 5/1723 |
| | | | 604/504 |
| 2010/0174228 A1 | 7/2010 | Buckingham et al. | |
| 2010/0211003 A1 * | 8/2010 | Sundar | A61M 5/16813 |
| | | | 604/67 |
| 2010/0228110 A1 | 9/2010 | Tsoukalis | |
| 2010/0262117 A1 | 10/2010 | Magni et al. | |
| 2010/0262434 A1 | 10/2010 | Shaya | |
| 2010/0298765 A1 | 11/2010 | Budiman et al. | |
| 2011/0021584 A1 | 1/2011 | Berggren et al. | |
| 2011/0028817 A1 | 2/2011 | Jin et al. | |
| 2011/0190694 A1 * | 8/2011 | Lanier, Jr. | A61M 5/14216 |
| | | | 604/67 |
| 2011/0202005 A1 * | 8/2011 | Yodfat | A61M 5/1413 |
| | | | 604/151 |
| 2011/0218495 A1 * | 9/2011 | Remde | A61M 5/14248 |
| | | | 604/151 |
| 2011/0313680 A1 | 12/2011 | Doyle, III et al. | |
| 2012/0078181 A1 * | 3/2012 | Smith | A61M 5/14216 |
| | | | 604/152 |
| 2012/0101451 A1 * | 4/2012 | Boit | A61M 5/1424 |
| | | | 604/224 |
| 2012/0123234 A1 | 5/2012 | Atlas et al. | |
| 2012/0136336 A1 | 5/2012 | Mastrototaro et al. | |
| 2012/0203085 A1 | 8/2012 | Rebec | |
| 2012/0215087 A1 | 8/2012 | Cobelli et al. | |
| 2012/0225134 A1 | 9/2012 | Komorowski | |
| 2012/0232520 A1 | 9/2012 | Sloan et al. | |
| 2012/0282111 A1 * | 11/2012 | Nip | F04B 49/06 |
| | | | 417/48 |
| 2013/0158503 A1 | 6/2013 | Kanderian, Jr. et al. | |
| 2013/0231642 A1 | 9/2013 | Doyle, III et al. | |
| 2013/0261406 A1 | 10/2013 | Rebec et al. | |
| 2013/0317753 A1 * | 11/2013 | Kamen | G06F 19/3418 |
| | | | 702/19 |
| 2013/0338576 A1 * | 12/2013 | O'Connor | A61M 5/16854 |
| | | | 604/67 |
| 2014/0121635 A1 | 5/2014 | Hayter | |
| 2014/0180203 A1 | 6/2014 | Budiman et al. | |
| 2014/0180240 A1 | 6/2014 | Finan et al. | |
| 2014/0200559 A1 | 7/2014 | Doyle, III et al. | |
| 2014/0278123 A1 | 9/2014 | Prodhom et al. | |
| 2015/0018633 A1 | 1/2015 | Kovachev et al. | |
| 2015/0025329 A1 | 1/2015 | Amarasingham et al. | |
| 2015/0025495 A1 | 1/2015 | Peyser | |
| 2015/0213217 A1 | 7/2015 | Amarasingham et al. | |
| 2015/0306314 A1 | 10/2015 | Doyle, III et al. | |

(56) References Cited

U.S. PATENT DOCUMENTS

| | | | |
|---|---|---|---|
| 2016/0082187 A1 | 3/2016 | Schaible et al. | |
| 2016/0256087 A1* | 9/2016 | Doyle, III | A61B 5/7235 |
| 2016/0287512 A1 | 10/2016 | Cooper et al. | |
| 2017/0143899 A1 | 5/2017 | Gondhalekar et al. | |
| 2017/0156682 A1 | 6/2017 | Doyle, III et al. | |
| 2017/0173261 A1* | 6/2017 | O'Connor | A61M 5/14248 |
| 2017/0189625 A1* | 7/2017 | Cirillo | A61M 5/20 |
| 2018/0036495 A1* | 2/2018 | Searle | A61M 5/482 |
| 2018/0204636 A1* | 7/2018 | Edwards | G16H 40/67 |
| 2018/0277253 A1 | 9/2018 | Gondhalekar et al. | |

FOREIGN PATENT DOCUMENTS

| | | |
|---|---|---|
| WO | 2012178134 A2 | 12/2012 |
| WO | 2014109898 A1 | 7/2014 |
| WO | 2014110538 A1 | 7/2014 |
| WO | 2015073211 A1 | 5/2015 |
| WO | 2016022650 A1 | 2/2016 |
| WO | 2017004278 A1 | 1/2017 |

OTHER PUBLICATIONS

Dassau et al., "Real-Time Hypoglycemia Prediction Suite Using Continuous Glucose Monitoring," Diabetes Care, vol. 33, No. 6, 1249-1254 (2010).

International Search Report and Written Opinion for International application No. PCT/US17/53262, dated Dec. 13, 2017 8 pages.

van Heusden, K. et al., "Control-Relevant Models for Glucose Control using A Priori Patient Characteristics" IEEE Transactions on Biomedical Engineering, vol. 59, No. 7, (Jul. 1, 2012) pp. 1839-1849.

Doyle III, et al., "Run-to-Run Control Strategy for Diabetes Management." Paper presented at 23rd Annual International Conference of the IEEE Engineering in Medicine and Biology Society, Istanbul, Turkey.(Oct. 2001).

Bequette, B.W., and Desemone, J.,"Intelligent Dosing System": Need for Design and Analysis Based on Control Theory, Diabetes Technology and Therapeutics 6 (6): 868-873 (2004).

Parker, R.S., et al., "A Model-Based Agorithm for Blood Gucose Control in Type I Diabetic Patients." IEEE Transactions on Biomedical Engineering, 46 (2) 148-147 (1999).

Anonymous: "Artificial pancreas—Wikipedia",Mar. 13, 2018 (Mar. 13, 2018), XP055603712, Retrieved from the Internet URL: https://en.wikipedia.org/w/index.php?title=Artificial pancreas&oldid=830262141#cite_note-9 [retrieved on Jul. 9, 2019] section "Medical Equipment" and the figure labeled "The medical equipment approach to an artificial pancreas".

International Search Report and Written Opinion for the International Patent Application No. PCT/US2019/055862, dated Mar. 11, 2020, 20 pages.

\* cited by examiner

FLUID DELIVERY DEVICE WITH SENSOR

CROSS-REFERENCE TO RELATED APPLICATIONS

This application claims the benefit of U.S. Provisional Application No. 62/398,792, filed Sep. 23, 2016, which is incorporated herein by reference in its entirety.

TECHNICAL FIELD

Embodiments generally relate to medication delivery. More particularly, embodiments relate to wearable drug delivery devices configured to monitor medication flow.

BACKGROUND

Drug delivery devices (e.g., infusion devices or pumps) can experience conditions that can lead to under-delivery or over-delivery of an infusate into a patient. For example, blockages in a fluid path (e.g., as caused by an occlusion) can cause a backup of fluid within the pump and a subsequent increase in fluid path pressure. When a blockage clears, the pressurized infusate can be delivered in a single bolus in an undesirable or unintended manner.

When air is trapped in the fluid path, changes in atmospheric pressure can cause the trapped air to expand or compress and to displace (e.g., by suction) fluid into or out of the patient. These situations can also cause under-delivery or under-delivery of the infusate into the patient. Swimming or flying are examples of common activities engaged in by a patient that can result in under-delivery and over-delivery without the patient's knowledge.

Additionally, when air is trapped in the fluid path, changes in ambient temperature can also cause the trapped air to expand or compress and to displace fluid into or out of the patient. Similarly, these situations can also cause under-delivery or over-delivery of the infusate into the patient. Swimming in the ocean or swimming in an unheated pool or using a heated blanket are examples of common activities engaged in by a patient that can result in under-delivery and over-delivery of the infusate without a patient's knowledge.

Many conventional drug delivery devices including infusion devices or pumps detect occlusions by monitoring the time it takes for the pump to actuate. This conventional approach can produce erroneous results based on variabilities within the drive system (e.g., due to friction, power sagging, mechanical variability of parts, etc.).

Even conventional systems that directly measure the pressure within the pump fluid path often do not detect changes in atmospheric pressure which can lead to over-delivery and under-delivery. These conventional systems typically utilize pressure sensors which measure pressure relative to atmospheric pressure and are incapable of detecting any change in atmospheric pressure which can lead to over-delivery and under-delivery without a patient's knowledge as described above.

Accordingly, what is needed is a drug delivery device with improved capabilities for detecting under-delivery and over-delivery conditions during intended delivery periods or unintended delivery periods that can be caused by a variety of factors including changes in atmospheric pressure.

DETAILED DESCRIPTION

Figure 1:
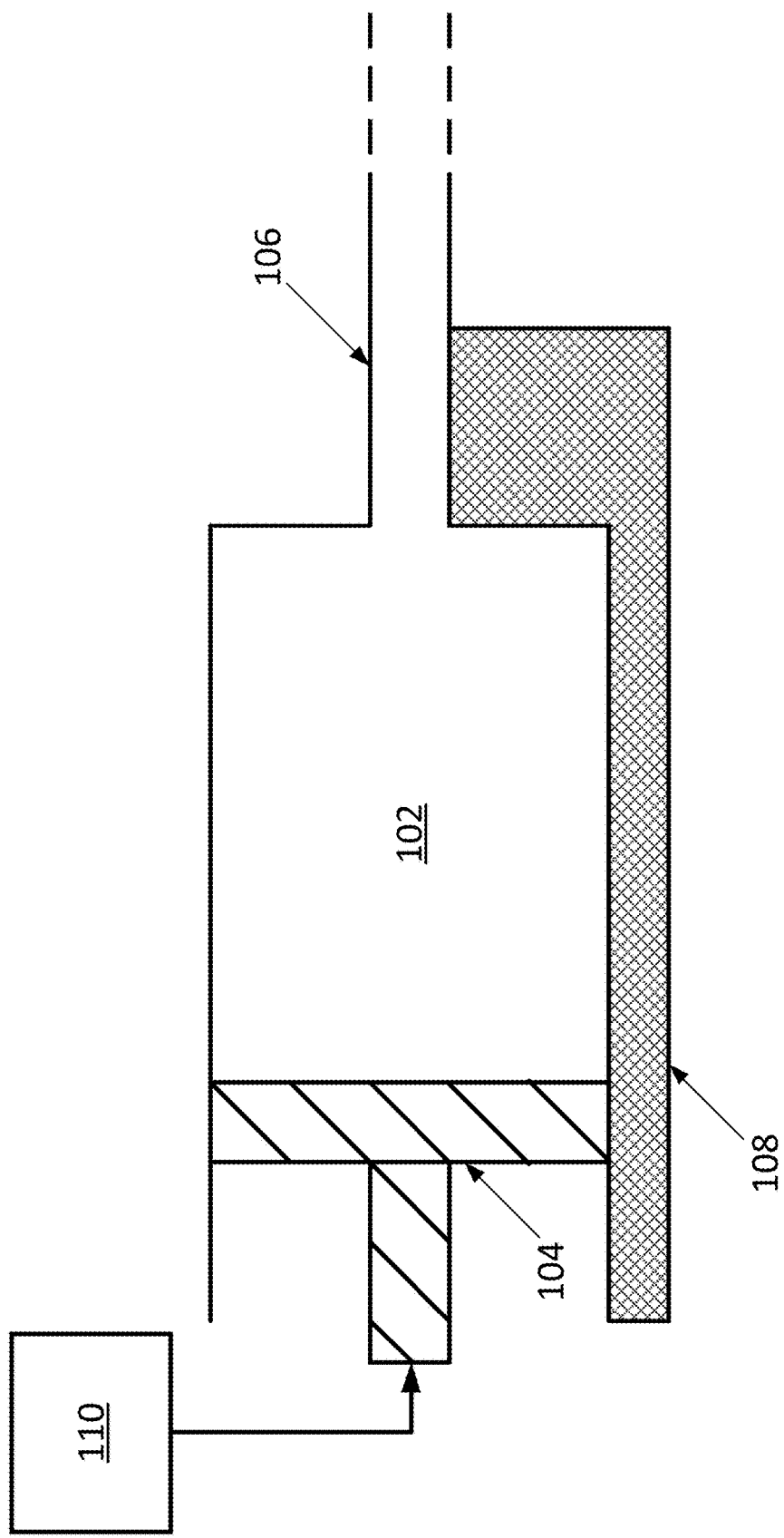
FIG. 1 illustrates a first exemplary pump system.

This disclosure presents various systems, components, and methods related to a drug delivery device. Each of the systems, components, and methods disclosed herein provides one or more advantages over conventional systems, components, and methods.

Various embodiments include a wearable drug delivery device having a pump system. The pump system can be used to deliver a stored liquid drug or other therapeutic agent to a user or patient. An absolute pressure sensor can be positioned within the fluid path of the drug delivery device and/or pump system. The absolute pressor sensor can detect both ambient pressure (e.g., absolute or atmospheric pressure) and relative pressure (gage or pumping pressure). Based on the detected pressures, the effects of external ambient pressure on air with the pump system and/or fluid path can be determined during intended drug delivery events and unintended drug delivery events. In turn, under-delivery and/or over-delivery of the liquid drug can be determined. Based on the severity of the determined under-delivery or over-delivery of the liquid drug, alarms of different urgencies can be provided to the user. Other embodiments are disclosed and described including various embodiments directed to the use of a flow sensor to detect the aforementioned over-delivery and under-delivery conditions.

Various embodiments provide techniques for monitoring the absolute and relative pressures associated with a liquid drug pump system of a wearable drug delivery device. Based on the monitored pressures, an amount (e.g., corresponding to an over-delivery or an under-delivery) and direction (e.g., into or out of the pump system) of unintended liquid drug flow can be determined. If the amount of the unintended liquid drug exceeds one or more thresholds, one or more associated alarms can be provided to a user. Monitoring can be provided during intended drug delivery operations when the pump system is directed to provide the liquid drug to the user and during unintended drug delivery operations when the pump system is directed to not provide the liquid drug to the user. Other embodiments are disclosed and described.

The pressure sensor 202 can be an absolute pressure sensor that can detect both ambient pressure (e.g., absolute or atmospheric pressure) and relative pressure (e.g., gage or pumping pressure) introduced as the pump system 200 displaces fluid (e.g., the infusate stored in the reservoir 102) in the overall fluid path of the pump system (e.g., including the reservoir 102 and the fluid path component 106). By using an absolute pressure sensor as the pressure sensor 202, it is possible to measure the effects of external ambient pressure on air within the reservoir 102. Further, by using an absolute pressure sensor as the pressure sensor 202, it is possible to measure the effects of the internal pumping pressure changes due to pumping (e.g., expelling the infusate from the reservoir 102 for delivery to the patient). By measuring these effects, the pump system 200 can detect situations of possible over-delivery and/or under-delivery of the infusate to the patient due to both intended and unintended actions (e.g., during periods of intended delivery and periods of unintended delivery). Further, the pump system 200 can provide indications of such over-delivery and/or under-delivery conditions or situations to the patient, allowing the patient to respond accordingly.

FIG. 1 illustrates a pump system that can be used to deliver an infusate to a patient. The pump system can include a reservoir 102, a plunger 104, a fluid path component 106, a supporting mechanical structure or component 108, and a plunger or pump drive mechanism 110. The reservoir 102 can store or hold the infusate. The infusate can be any liquid drug and/or therapeutic agent. The plunger 104 can be used to expel the infusate from the reservoir 102 for delivery to a patient or user. The reservoir 102 can be coupled to the fluid path component 106. The fluid path component 106 can be coupled to the patient.

The supporting mechanical structure 108 can provide structural support to the reservoir 102, the fluid path component 106, and/or the plunger drive mechanism 110. The supporting mechanical structure 108 is not limited to the presentation depicted in FIG. 1. The supporting mechanical structure 108 can encase, surround, or otherwise provide structural support for the reservoir 102, the fluid path component 106, and/or the plunger drive mechanism 110. The plunger drive mechanism 110 can be any mechanical or electromechanical system that can advance the plunger 104 into the reservoir 102. As the plunger drive mechanism 110 is operated and the plunger 104 advances into the reservoir, the infusate can be expelled from the reservoir 102 and provided to the patient by way of the fluid path component 104. The fluid path component 106 can include or can be coupled to a needle or cannula providing access (e.g., via an outlet) to the patient.

The pump system shown in FIG. 1 can be part of a drug delivery device. As an example, the pump system can be part of a wearable drug delivery device. In various embodiments, the pump system can be used to deliver insulin to a patient. The pump system can be considered to be an infusion pump system. The overall fluid path of the pump system shown in FIG. 1 can include the reservoir 102 as well as the fluid path component 106 that couples the reservoir 102 to the patient.

During periods of operation—for example, when the pump system of FIG. 1 is specifically directed to deliver a portion of the infusate to the patient—the pump system can erroneously over-deliver or under-deliver a desired amount of infusate to the patient. Under-delivery and over-delivery can be caused by a variety of factors including changes in atmospheric pressure, changes in ambient temperature, and occlusions in the fluid path. Further, during periods of unintended delivery—for example, when the pump system of FIG. 1 is specifically directed not to deliver any infusate to the patient—these factors can still cause delivery of unintended amounts of the infusate to the patient (or backflow of the infusate).

The pump system shown in FIG. 1 does not include any capability to detect and monitor any over-delivery or under-delivery of the infusate during intended delivery periods or unintended delivery periods. The pump system of FIG. 1 is further unable to account for any such under or over-delivery condition and is incapable of notifying the patient as to any under or over-delivery condition. Consequently, operation and of the pump system of FIG. 1 can be inefficient and even hazardous to the patient.

Figure 2:
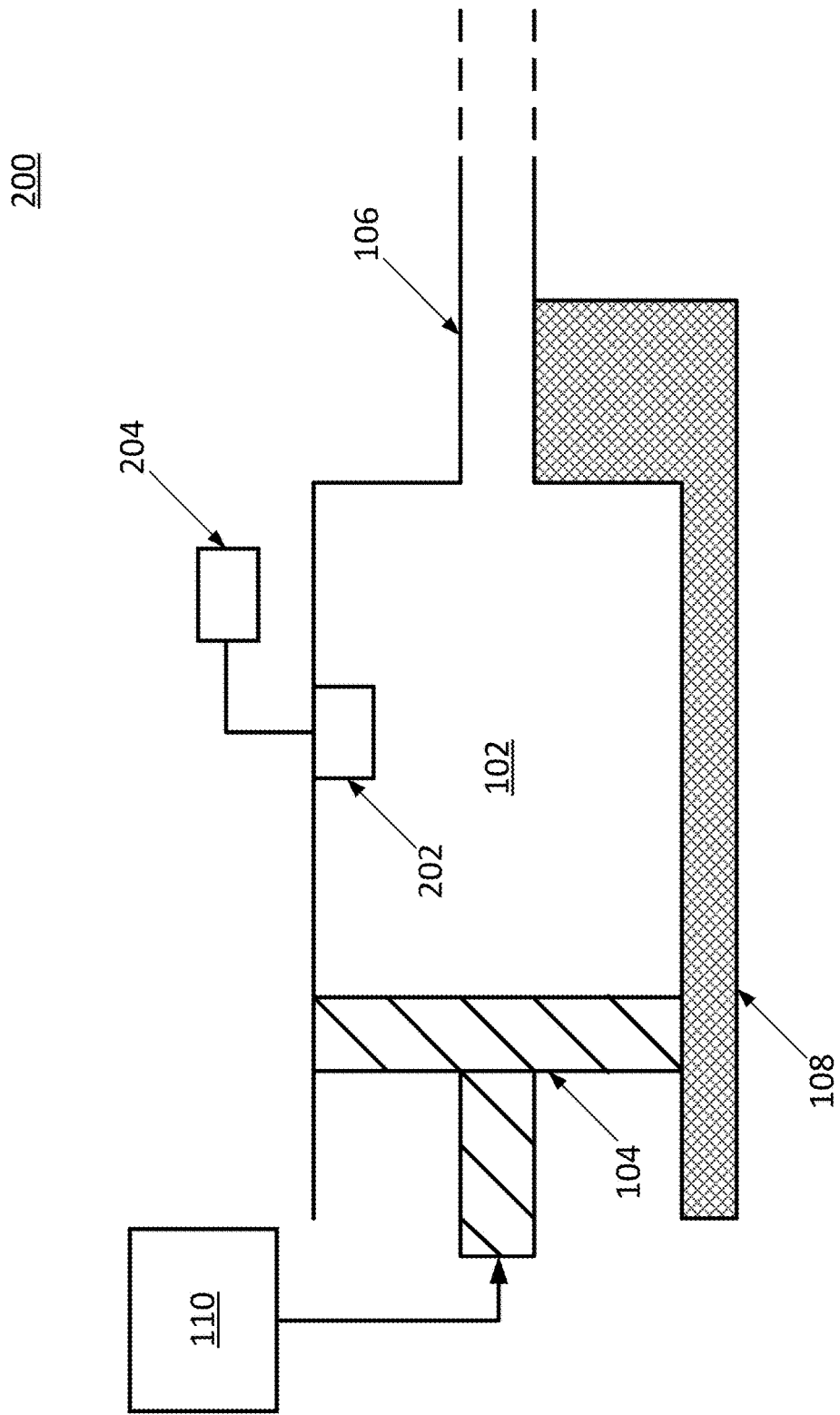
FIG. 2 illustrates a second exemplary pump system incorporating a pressure sensor.

FIG. 2 illustrates a pump system 200 (or infusion pump system 200) for providing monitoring of any over-delivery or under-delivery condition during any intended or unintended drug delivery. As shown in FIG. 2, the pump system 200 can include the reservoir 102, the plunger 104, the fluid path component 106, the supporting component 108, and the plunger drive mechanism 110. The pump system 200 can further include a pressure sensor 202 and a monitoring component 204. The pump system 200 can, among other features, detect flow (e.g., unintended flow) of the infusate through pressure sensing as described herein.

The pressure sensor 202 can be an absolute pressure sensor that can detect both ambient pressure (e.g., absolute or atmospheric pressure) and relative pressure (e.g., gage or pumping pressure) introduced as the pump system 200 displaces fluid (e.g., the infusate stored in the reservoir 102) in the overall fluid path of the pump system (e.g., including the reservoir 102 and the fluid path component 106). By using an absolute pressure sensor as the pressure sensor 202, it is possible to measure the effects of external ambient pressure on air within the reservoir 102. Further, by using an absolute pressure sensor as the pressure sensor 202, it is possible to measure the effects of the internal pumping pressure changes due to pumping (e.g., expelling the infusate from the reservoir 102 for delivery to the patient). By measuring these effects, the pump system 200 can detect situations of possible over-delivery and/or under-delivery of the infusate to the patient due to both intended and unintended actions (e.g., during periods of intended delivery and periods of unintended delivery). Further, the pump system 200 can provide indications of such over-delivery and/or under-delivery conditions or situations to the patient, allowing the patient to respond accordingly. This enables a drug delivery device that incorporates the pump system 200 to operate more effectively and safely and to provide an improved experience for the patient.

In various embodiments, the pressure sensor 202 can be integrated into the reservoir 102 as shown in FIG. 2. In various embodiments, the pressure sensor 202 can be integrated anywhere along the overall fluid path of the pump system 200 (e.g., including the reservoir 102 and/or the fluid path component 106) that is at the same approximate pressure as the outlet into the patient. An intervening membrane (not shown in FIG. 2 for simplicity) can be used to isolate the pressure sensor 202 from the infusate within the reservoir 102 and/or fluid path component 106. Alternatively, a pliable gel or sufficiently soft rubber can be used to isolate the pressure sensor 202 from the infusate.

In various embodiments, the pressure sensor 202 can have a round body to simplify sealing against the reservoir 102 and/or the fluid path component 106. In various embodiments, an integral lip seal can be used to seal the interface between the body of the pressure sensor 202 and the reservoir 102 and/or fluid path component 106.

The pressure sensor 202 can be coupled to a monitoring component 204. The pressure sensor 202 can measure the absolute pressure of the reservoir 102 and/or the fluid path component 106 (e.g., the overall fluid path of the pump system 200) and can provide an output signal to the monitoring component 204. In various embodiments, the pressure sensor 202 can take continuous readings of the absolute pressure. The output signal from the pressure sensor 202 can indicate the measured or detected absolute pressure and/or any other measured, detected, or derived pressure value.

The monitoring component 204 can process the received signal from the pressure sensor 202. The monitoring component 204 can be implemented in hardware, software, or any combination thereof. In various embodiments, the monitoring component 204 can be implemented using a processor and associated memory and can execute one or more monitoring algorithms or processes as described herein. In various embodiments, the monitoring component 204 can be implemented as dedicated hardware (e.g., as an application specific integrated circuit (ASIC)). The monitoring component 204 can be a constituent part of the pump system 200, can be implemented in software as a computational model, or can be implemented external to the pump system 200 (e.g., remotely).

In various embodiment, the output signal generated by the pressure sensor 202 can be a voltage signal, a current signal, and/or an electrical charge signal. In various embodiment, the output signal generated by the pressure sensor can be a data signal (e.g., an analog or digital data signal) such as, for example, an inter-integrated circuit (I2C), serial peripheral interface (SPI), or any other known or customized synchronous or asynchronous data communication stream. In general, the output signal from the pressure sensor 202 can indicate a measured pressure. Further, the pressure sensor 202 and the monitoring component 204 can communicate over any known signaling protocol or standard including any known wired or wireless communication or signaling protocol. In various embodiments, the signal generated by the pressure sensor 202 for output and delivery to the monitoring component can be temperature compensated to remove or mitigate any error due to temperature changes. The monitoring component 204 can convert the signal received from the pressure sensor 202 into an indication of absolute pressure (e.g., pounds per square inch absolute (psia)).

The monitoring component 204 can generate a characterization of the fluid capacitance of the reservoir 102 and/or the fluid path component 106 (e.g., a model of the fluid capacitance of the overall fluid path of the pump system 200). Alternatively, the monitoring component 204 can be provided such information. For example, the monitoring component 204 can include a memory component or can access a memory component storing such information. In various embodiments, one or more components (e.g., external hardware components) can be used to generate characterizations of the fluid path fluid capacitance that can be provided to the monitoring component 204 in the form of data that can be stored, or integrally included as part of operational software. The characteristic fluid capacitance can be an input into a detection algorithm or monitoring process implemented by the monitoring component 204. The fluid capacitance can be considered to be the relationship between an internal pressure of the reservoir 102 and/or the fluid path component 106 (e.g., the overall fluid path of the pump system 200) and the volume of fluid necessary to achieve the specific pressure.

As will be appreciated by a person of ordinary skill in the art, the nature of fluid capacitance is roughly equivalent to electrical capacitance in which the infusate acts as electrical charge, internal gage pressure behaves as the positive voltage in an electrical circuit, the hydraulic stiffness of a fluid path acts as the electrical capacitance of a capacitor, and the fluid path outlet flow restriction acts as a resistor does in the electrical equivalent. Additionally, counter infusion pressure provided by the patient at the infusion site acts as the ground potential. Further, when counter-infusion pressure matches the infusion pressure, flow (e.g., to the patient) stops. If counter-infusion pressure exceeds internal gage pressure, counter flow (flow into the fluid path of the pump system 200 and away from the patient) can occur.

The fluid capacitance can be characterized using a numeric value, or a range of numeric values, or a variable model which defines the characteristic fluid capacitance of the overall fluid path of the pump system 200. In various embodiments, a memory associated with the monitoring component 204 can store values for characterizing the fluid capacitance associated with the pump system 200. In various embodiments, the one or more stored values can be based on characterization of the specific design of the pump system 200.

As the pump system 200 operates to expel the infusate from the reservoir 102 and into the fluid path component 106 for delivery to the patient, the fluid capacitance associated with the pump system 200 can change. For example, the fluid capacitance can change based on changes to the effective stiffness of the reservoir 102 as the plunger 104 is advanced further into the reservoir 102 by the plunger drive mechanism 110. As another example, changes in the stiffness of the supporting mechanical structure 108, the pump drive mechanism 110, or the interfaces between these components can cause the fluid capacitance to change. Accordingly, the monitoring component 204 can include a range of characterized fluid capacitance values that account for any such change. In various embodiments, the monitoring component 204 can be configured to use a function or other mathematical model capable of defining the change in fluid capacitance over the range of operation of the pump system 200—for example, from fully filled to empty. Based on an indication of the fluid capacitance—for example, by generating an estimate of the fluid capacitance over time as the pump system 200 operates—the monitoring component 204 can detect and determine, for example, any under-delivered fluid based on an indication of pressure provided by the pressure sensor 202.

By monitoring the absolute pressure within the fluid path of the pump system 200, the amount and direction of flow from the fluid path of the pump system 200 can be determined by the monitoring component 204. Based on determined changes in the pressure of the fluid path of the pump system 200, and the characteristic fluid capacitance of the fluid path of the pump system 200, a total net flow of fluid (e.g., the infusate) from a first point in time to a later, second point in time can be determined. Based on the amount and direction of flow error over time (e.g., unintended or undesired flow of the infusate into or out of the fluid path of the pump system 200), the monitoring component 204 can determine if an alert or other alarm should be issued to the patient.

During operation of the pump system 200, as the plunger 104 advances further into the reservoir 102, the fluid capacitance associated with the pump system 200 can change and the pressure associated with the pump system 200 can also change. The monitoring component 204, by monitoring the pressure and fluid capacitance of the pump system 200 over time, can determine net fluid flow over time—either intended or unintended and either into or out of the pump system 200 (or a drug delivery device in which the pump system 200 can be included). In various embodiments, to estimate an amount of fluid flow, the monitoring component 200 can estimate an amount of undelivered volume of fluid (e.g., the infusate within the fluid path or reservoir 102) at two different points in time.

Accordingly, based on data or information provided by the pressure sensor 202, the monitoring component 204 can monitor an amount of infusate delivered over time to determine if the amount is a proper or correct amount based on a predetermined level of intended infusate delivery. The monitoring component 204 can further determine if changes in physical conditions or the environment in which the pump system 200 operates can lead to under-delivery or over-delivery of the infusate during periods of delivery or non-delivery. The flow direction and the amount of fluid as determined by the monitoring component 204 can be compared to one or more operational thresholds, to determine if an alert should be issued to the patient. This allows the patient to more safely use the pump system 200 and to take corrective action if necessary.

In various embodiments, the pump system 200 and/or the monitoring component 204 can operate to monitor the following operational conditions (e.g., errors) associated with the pump system:

1. Deviation in total infusate delivered (e.g., from a desired level of infusate to be delivered) during an intended delivery period/delivery operation;
2. Deviation in total infusate delivered over time from unintended delivery/non-intended delivery operation; and Further, in various embodiments, the pump system 200 and/or the monitoring component 204 (and/or a drug delivery device of which the pump system 200 can be a component) can operate to provide the following alarms as necessary based on monitoring flow direction and amount of flow:

1. Under-delivery of the infusate during pumping—can be caused by, for example, a partial occlusion in the fluid path of the pump system 200, increased back pressure, and/or decreased site viability;
2. No delivery of the infusate during pumping—can be caused by, for example, a full occlusion in the fluid path of the pump system 200 and an alarm can alert the patient to immediately replace the drug delivery device in which the pump system 200 operates;
3. Potential back-flow into pump system 200 delaying delivery—can be caused by, for example, ambient pressure changes from low pressure to high pressure (e.g., during landing in a flight); and
4. Potential out-flow from pump system 200 without pumping—can be caused by, for example, ambient pressure changes from high pressure to low pressure (e.g., during take-off in a flight).

For the first source of error listed above (i.e., deviation of total infusate delivered over time from intended delivery), the monitoring component 204 can monitor (e.g., continuously) the pressure in the fluid path of the pump system 200 from the start of an intended delivery event until the end of the intended delivery event during which, for example, a predetermined or desired amount of infusate is to be delivered. The monitoring component 204 can then compare the difference in the determined pressures (or the volume of undelivered fluid) to predetermined delivery thresholds. If the amount of infusate delivered is more than desired or intended, and exceeds a first threshold, then an alert or alarm can be provided to the user. If the amount of infusate delivered is less than desired or intended, and is less than a second threshold, then an alert or alarm can similarly be provided to the user. In this way, a patient can be made aware of under-delivery or over-delivery situations through pressure monitoring that enables flow amounts and directions to be determined.

In various embodiments, the alerts or alarms can be visual and/or audible and can include haptic and/or tactile feedback such as vibrational movement of the drug delivery device. Further, in various embodiments, the alarms can vary based on the type of alarm—for example, a first type of visual and/or audible alert for an over-delivery condition and a second, different visual and/or audible alert for an under-delivery condition. If the over or under-delivery condition stays within the set thresholds, then an alarm may not be provided (e.g., if the deviation from a desired delivery is minimal). Further, multiple thresholds can be established and compared such that more significant deviations from an intended delivery can trigger heightened alarm signals or indications or the patient.

In various embodiments, the thresholds can be dynamically adjusted. For example, the thresholds for comparison can be adjusted based on a de-rating factor that can be based on the total delivered amount of infusate and/or the current unmetabolized excess infusate remaining in the blood stream in the event of an over-delivery event. In various embodiments, the monitoring component 204 can determine an estimate of infusate yet to be delivered in the event of under-delivery by monitoring the capacity of fluid path pressure differential from the start of infusion.

In various embodiments, the monitoring component 204 can distinguish changes in pressure due to ambient (atmospheric) pressure changes from intended pumping pressure changes. In various embodiments, the monitoring component 204 can implement various filtering techniques including, for example, Bayesian nonlinear filters such as Kalman and/or particle filters to isolate and then compensate for random wandering pressure changes due to, for example, changing weather conditions. The monitoring component 204 can also employ band pass filtering to isolate pulsatile pumping pressure changes.

Atmospheric pressure can change with geographic location (e.g., altitude) as well as weather. Accordingly, the monitoring component 204 can include a rolling window filter for establishing or re-establishing a baseline atmospheric pressure. This baseline atmospheric pressure level can be used for comparison over any time period. In various embodiments, the baseline filter window implemented by the monitoring component 204 can be linked to the metabolization rate of the infusate when known which can be provided to the monitoring component 204.

As described above, the monitoring component 204 can include one or more thresholds and associated alarms that can be issued to a user. Further, as described above, multiple threshold levels and heightened alerts can be used for comparison to indicate an escalating intensity of alarm based on the degree of risk associated with any particular threshold being exceeded or not met—for example, based on the level of infusate delivery missed or the level of excessive infusate delivery.

In various embodiments, in the case of little to no delivery (e.g., due to an occlusion), thresholds can be set based on the specific risk of the infusate via a table of values stored in a memory (e.g., ROM and/or RAM memory or any other memory or look-up table) associated with the monitoring component 204

For the second source of error listed above (i.e., deviation of total infusate delivered over time from unintended delivery), the following can be contributing sources for any such deviation or error:

1. Expansion or contraction of air within the fluid path of the pump system 200 due to ambient pressure or temperature changes;
2. Physical compression of the fluid path of the pump system 200;
3. Unintended operation of the plunger 104 and/or pumping mechanism of the pump system 200;
4. Mechanical errors (e.g., incorrect drive train multiplier, thread errors, or cam errors); and
5. Siphoning due to air leaks in the fluid path of the pump system 200.

In various embodiments, the monitoring component 204 can monitor (e.g., sample) the pressure of the fluid path of the pump system 200 continuously (or semi-continuously to conserve power) during periods of intended non-delivery—that is, during times when the pump system 200 is not being directed to specifically provide the infusate to the patient. During these periods, the internal pressure of the fluid path of the pump system 200 is unlikely to change by more than an expected amount due to the narrow range of atmospheric pressure changes. By monitoring the fluid path pressure of the pump system 200, the monitoring component 204 can determine if any such changes in pressure are significant.

In situations where the atmospheric pressure can change by an amount more than an expected amount due to normal weather based atmospheric pressure (e.g., during flying on a commercial flight), the monitoring component 204 can determine the potential unintended delivery due to air expansion in the reservoir 104 and can alert the user to any potential risk associated with such determined unintended delivery. Additionally, the monitoring component 204 can alert the user of the opposite condition (e.g., back flow) that may occur following an increase in absolute pressure as would be experienced during normalization of aircraft cabin pressure upon landing during a flight.

Further, in situations where the atmospheric pressure can change by an amount more than an expected amount due to normal weather based atmospheric changes, but at a rate which is lower than typical air travel pressure changes (e.g., traversing altitude slowly as can happen when driving from a lower altitude to a higher altitude), the monitoring component 204 can determine the rate of change of atmospheric pressure. The monitoring component 204 can use this determined rate to properly adjust the intensity of alerts and/or alarms provided to the patient.

Overall, the monitoring component 204 can monitor pressure changes during periods of non-delivery (e.g., intended non-delivery) to determine if any fluid is unintentionally provided to the patient or being removed from the fluid path coupled to the patient. If the levels of unintended delivery exceed one or more thresholds during such periods, one or more associated alarms (e.g., of heightened intensity) can be provided to the user.

In various embodiments, the monitoring component 204 can use a rolling window low pass filter matched to the in vivo decay rate of the infusate within the patient's body, or based on a reasonable threshold which can be set by the user. Additional filtering techniques can be employed in other embodiments utilizing Kalman, particle, or non-linear filtering techniques.

In various embodiments, the pump system 200 can include a temperature sensor to alter the sampling frequency in response to the potential for expansion or contraction of air bubbles in the fluid path of the pump system 200. For example, if greater temperature swings are to be expected within the environment in which the pump system 200 operates, larger pressure swings may be expected to occur. Accordingly, monitoring and/or sampling of the pressure may be adjusted during such time periods to increase monitoring or sampling. The temperature sensor can be part of or can be coupled to the monitoring component 204 to provide a measure of temperature to the monitoring component 204.

Figure 3:
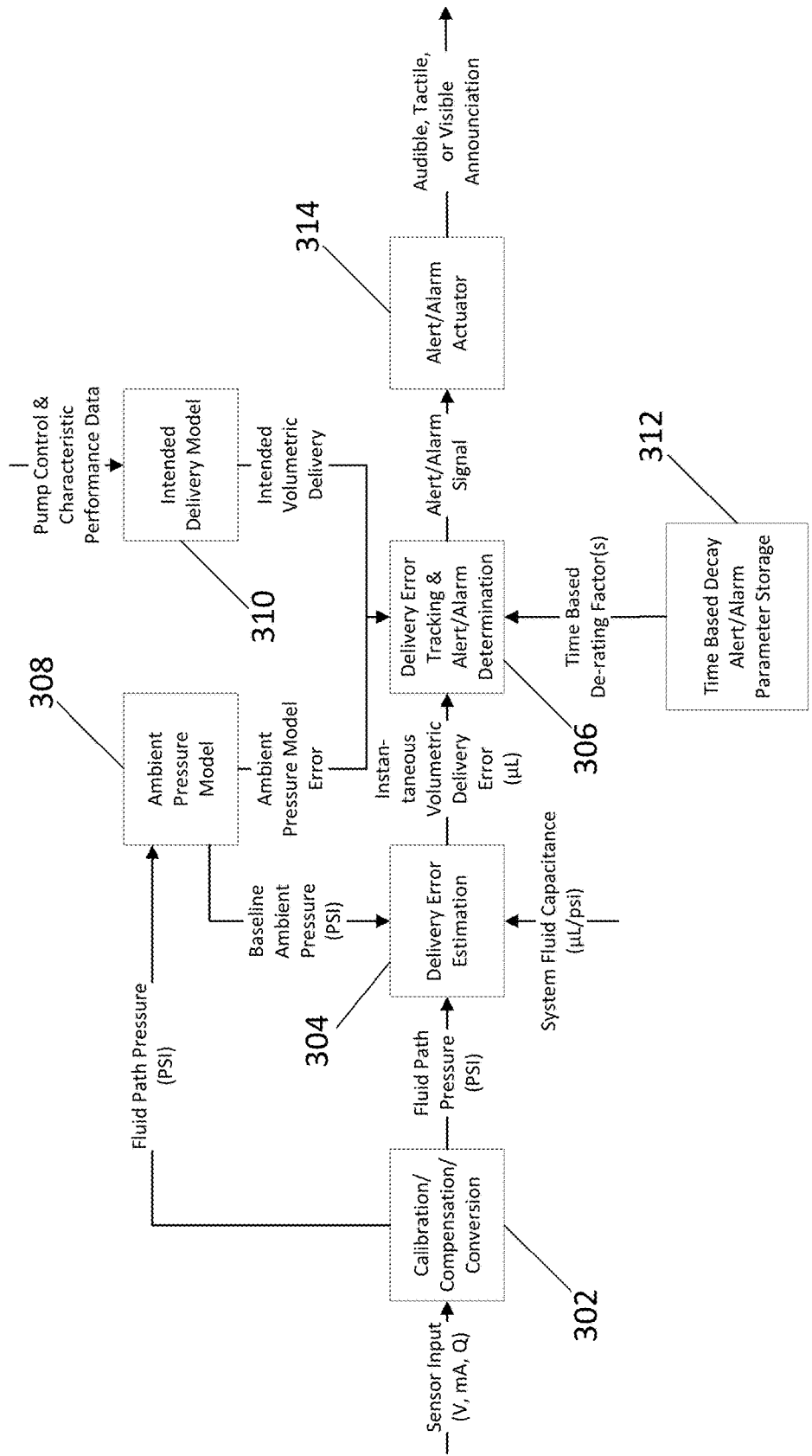
FIG. 3 illustrates a block diagram of operations performed by the pump system of FIG. 2.

FIG. 3 illustrates an operational block diagram 300 that shows operations for providing monitoring of any over-delivery or under-delivery condition during any intended or unintended drug delivery based on the pressure sensing described herein.

The operational block diagram 300 illustrates components that can be implemented by or can be included within the monitoring component 204 when implemented in conjunction with the pressure sensor 202. The operational block diagram 300 illustrates the inputs and outputs of each component and the function or capabilities of each components. The operations and components shown can be implemented in hardware, software, or any combination thereof.

The operational block diagram 300 can include the following components: a calibration-compensation-conversion component 302, a delivery error estimation component 304, a delivery error tracking and alarm determination 306, an ambient pressure model component 308, an intended delivery model 3108, a time-based decay alert-alarm parameter storage component 312, and an alert-alarm actuator component 314. The operations and functionalities of these components are described below.

The calibration-compensation-conversion component 302 can be coupled to a pressure sensor (e.g., the pressure sensor 202) and can receive one or more signals from the pressure sensor as described above. The calibration-compensation-conversion component 302 can also receive one or more signals relating to calibration, conversion, or compensation parameters. The calibration-compensation-conversion component 302 can operate to determine and output fluid path pressure (e.g., psi) based on the signals from the pressure sensor. Accordingly, the calibration-compensation-conversion component 302 can output a fluid path pressure signal. The calibration, conversion, or compensation parameters can also operate to provide sensor calibration and/or compensation functions such as, for example, linearization of output, input/output offset correction, and/or temperature compensation.

The delivery error estimation component 304 can receive the fluid path pressure output signal from the calibration-compensation-conversion component 302. The delivery error estimation component 304 can also receive fluid capacitance values (e.g., system calibration values) and baseline pressure values as shown in FIG. 3. The delivery error estimation component 304 can operate to determine instantaneous volumetric delivery error (e.g., an amount of under-delivery or over-delivery) and can output a signal indicating the same. To determine the instantaneous volumetric delivery error, the delivery error estimation component 304 can transform the provided pressure level relative to the pressure baseline into a delivery error by multiplying the pressure difference by the provided fluid capacitance value.

In various embodiments, to determine instantaneous volumetric delivery error, which can be represented as Verror(t), where "t" represent time, the delivery error estimate estimation component 304 can utilize a fluid capacitance value or values, which can be represented as Cfluid($\xi$,t). Fluid capacitance is typically expressed in units of volume/pressure (e.g., in μL/psi for small pumping devices). "$\xi$" can represent an aggregated variability of the fluid capacitance which can vary both with time and with any number of system physical parameters (e.g., specific to each pumping device). The baseline ambient pressure, represented as P0(t), can be the baseline pressure at which the system is operating at any given time as provided by the ambient pressure model 308. The instantaneous fluid path pressure provided by the calibration-compensation-conversion component 302, represented as P(t), can be the instantaneous pressure measured at a given time. The instantaneous volumetric delivery error can therefore be expressed as: Verror(t)=[P(t)−P0(t)]*Cfluid (ξ,t).

The delivery error tracking and alarm determination component 306 can receive the instantaneous volumetric delivery error signal outputted by the delivery error estimation component 304. The delivery error tracking and alarm determination component 306 can also receive time-based de-rating factors, an ambient pressure model error, and an indication of intended volumetric delivery as shown in FIG. 3. Based on these input signals, the delivery error tracking and alarm determination component 306 can generate an alert or alarm signal as necessary, as described above. The delivery error tracking and alarm determination component 306 can compare the intended volumetric delivery against the sum of ambient pressure model error and instantaneous volumetric delivery error as modified by time-based de-rating factors. Threshold comparisons can also be made to determine if an alarm signal should be generated. If an alarm condition is determined, a signal indicating the same can be generated and outputted.

The ambient pressure model 308 can receive the fluid path pressure signal from the calibration-compensation-conversion component 302. The ambient pressure model 308 can output an ambient pressure model error. The ambient pressure model 308 can track background ambient pressure changes to limit false alarms due to ambient pressure or back pressure changes. The ambient pressure model 308 can also track background ambient pressure changes to determine over-delivery and/or under-delivery due to significant pressure excursions.

The intended delivery model component 310 can receive pump control data (e.g., a count of the number of pulses delivered) and can receive pump characteristic performance data (e.g., a measure of volume per pulse delivery). The intended delivery model component 310 generate an indication of expected volumetric delivery as shown in FIG. 3. The intended delivery model component 310 can track the expected delivery as commanded by the pump system for comparison in the delivery error tracking and alert-alarm determination component 306.

The time-based decay alert-alarm parameter storage 312 can receive and/or store system alert-alarm decay parameters. The time-based decay alert-alarm parameter storage 312 can output specific mathematical functions to de-rate the impact of instantaneous volumetric error over time. The time-based decay alert-alarm parameter storage 312 can ensure transient unintended delivery events do not accumulate in the system and lead to unnecessary alarms.

The alert-alarm actuator 314 can receive any alert-alarm signal from the delivery error tracking and alarm determination component 306. Based upon receipt of any alert-alarm signal, the alert-alarm actuator 314 can activate an alarm mechanism or component as described above including, for example, a visual, tactile, and/or audible alarm to notify the user of an urgent condition.

Figure 4:
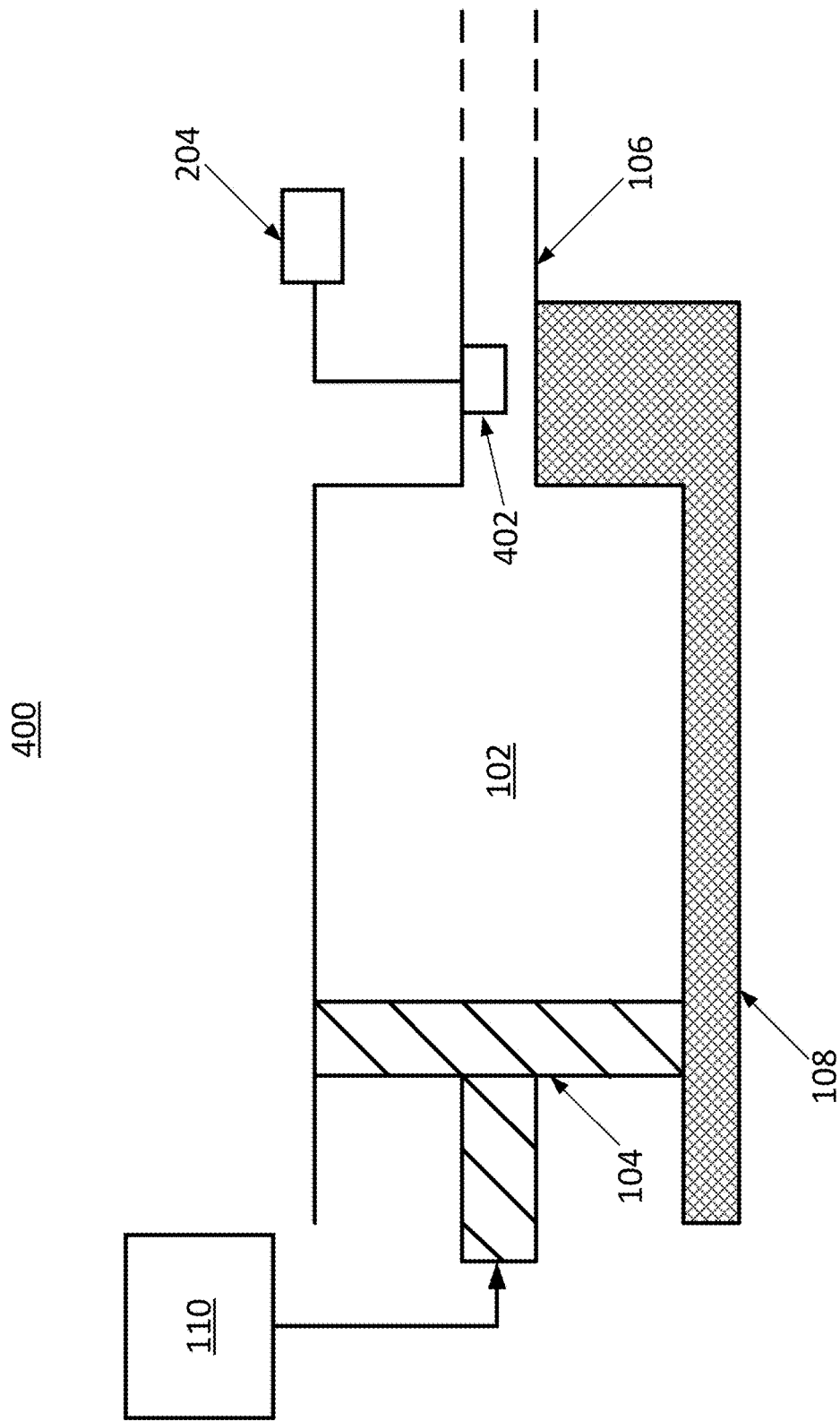
FIG. 4 illustrates a third exemplary pump system incorporating a flow sensor.

FIG. 4 illustrates a pump system 400 (or infusion pump system 400) for monitoring of any over-delivery or under-delivery condition during any intended or unintended drug delivery. As shown in FIG. 4, the pump system 400 can include the reservoir 102, the plunger 104, the fluid path component 106, a flow sensor 402, and the monitoring component 204. The pump system 400 can, among other features, detect unintended flow through flow sensing as described herein.

In contrast to the operation of the pump system 200 which can detect pressure and subsequently determine flow based on fluid capacitance of the fluid path of the pump system 200, the pump system 400 uses a flow sensor 402. The flow sensor 402 can be positioned directly in the flow path of the pump system 400 (e.g., in the fluid path component 106 as shown in FIG. 4). In various embodiments, the flow sensor 402 can sense flow (e.g., flow of the infusate) out of and into the fluid path of the pump system 400.

In general, the flow sensor 402 can be positioned anywhere along the fluid path of the pump system 400 including in a cannula coupled to the end of the fluid path component 106 leading to the patient. In various embodiments, the flow sensor 402 can be located just outside the reservoir 102 and before the hard cannula providing access to the patient. In various embodiments, the flow sensor 402 can be integrated into the hard cannula.

A variety of different types of flow sensors can be used for the flow sensor 402 such as, for example, a micro-electro-mechanical system (MEMS) thermal mass flow sensor, a paddle wheel, or other type flow sensor appropriately sized for the expected flow from the intended pumping action of the pump system 400 and/or the effect of ambient pressure changes on air trapped within the fluid path of the pump system 400.

The flow channel for the flow sensor 402 can be made from a variety of materials including, for example, glass, metal, or any other material that can provide adequate thermal conductance to detect changes in the thermal gradient in the flowing media (e.g., the infusate). The flow sensor 402 can be calibrated for the specific viscosity, thermal conductance, and flow channel convective coefficient, and external thermal changes (e.g., to provide temperature compensation).

The pump system 400 can provide similar functionality as the pump system 200 with the change of a flow sensor 402 being used instead of a pressure sensor as provided for in the pump system 200. To that end, the flow sensor 402 can be coupled to the monitoring component 204 with the monitoring component 204 configured to operate in conjunction with a flow sensor. The flow sensor 402 can take regular readings of flow through the fluid path of the pump system 400 and can output a signal to the monitoring component 204. The type of signal, format, and/or protocol of the signal of the output signal can be similar to the output signal provided by the pressure sensor 202 but with providing an indication of flow rather than pressure.

The monitoring component 204 can convert the signal from the flow sensor 402 to a measure of flow rate (e.g., in units of volume/time). In various embodiments, a flow rate in units of μL/minute can be used. In general, any representation of flow magnitude can be used.

To determine total flow over a given period of time, the monitoring component 204 can integrate the flow data to compute the total net volume dispensed over a given amount of time. This value of net total delivery can then be used to monitor over-delivery and/or under-delivery conditions during operation of the pump system 400 in a manner similar to that described above in relation to the pump system 200.

Accordingly, based on data or information provided by the flow sensor 402, the monitoring component 204 can monitor an amount of infusate delivered over time to determine if the amount is a proper or correct amount based on a predetermined level of intended infusate delivery. The monitoring component 204 can further determine if changes in physical conditions or the environment in which the pump system 400 operates can lead to under-delivery or over-delivery of the infusate during periods of intended delivery or intended non-delivery. The flow direction and the amount of fluid as determined by the monitoring component 204 can be compared to one or more operational thresholds, to determine if an alert should be issued to the patient. This allows the patient to more safely use the pump system 400 and to take corrective action if necessary.

Overall, the pump system 400 can monitor the same operation conditions and errors listed above in relation to the pump system 200 and can operate to provide the alarms indicated above as necessary based on monitoring flow direction and amount of flow during delivery periods and non-delivery periods (e.g., by monitoring net flow over set intervals of time of delivery or non-delivery). Accordingly, the discussion above of these features in relation to the pump system 200 are applicable to the pump system 400.

Further, the pump system 400 can adjust sampling of flow rates during (e.g., monitoring of flow rates) during periods of non-delivery—that is, during times when the pump system 400 is not being directed to specifically provide the infusate to the patient. Sampling of flow can be made continuously or semi-continuously to conserve power. In various embodiments, the pump system 400 can include an ambient pressure sensor to alter the flow sampling frequency in response to the potential for expansion or contraction of air bubbles in the fluid path. In various embodiments, the pump system 400—similar to the pump system 200—can include a temperature sensor to alter the flow sampling frequency in response to the potential for expansion or contraction of air bubbles in the fluid path, as described above in relation to the pump system 200.

Figure 5:
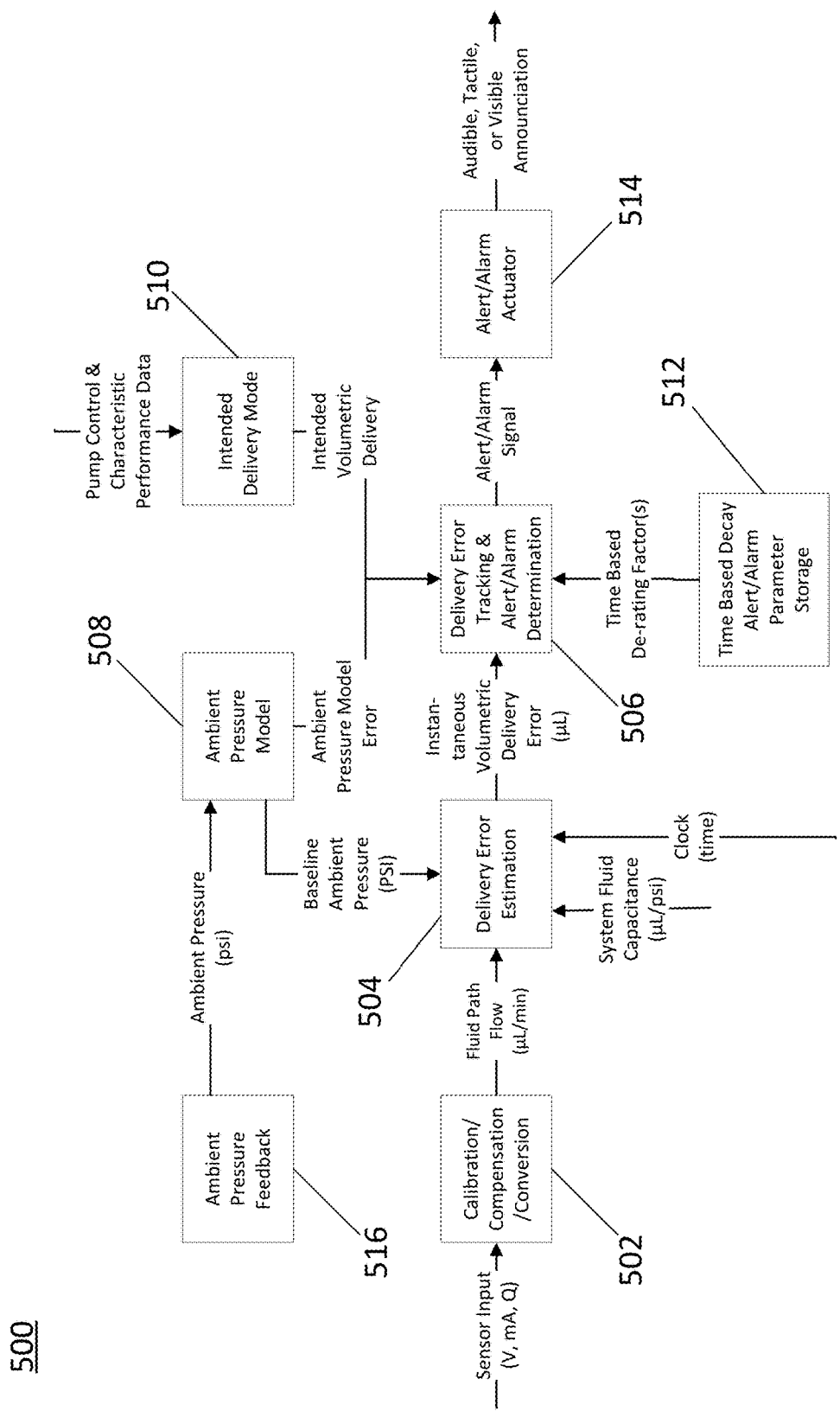
FIG. 5 illustrates a block diagram of operations performed by the pump system of FIG. 4.

FIG. 5 illustrates an operational block diagram 500 that shows operations for monitoring of any over-delivery or under-delivery condition during any intended or unintended drug delivery based on the flow sensing described herein. The operational block diagram 500 illustrates components that can be implemented by or can be included within the monitoring component 204 when implemented in conjunction with the flow sensor 402. The operational block diagram 500 illustrates the inputs and outputs of each component and the function or capabilities of each components. The operations and components shown can be implemented in hardware, software, or any combination thereof.

The operational block diagram 500 can include the following components: a calibration-compensation-conversion component 502, a delivery error estimation component 504, a delivery error tracking and alarm determination 506, an ambient pressure model component 508, an intended delivery model 510, a time-based decay alert-alarm parameter storage component 512, and an alert-alarm actuator component 514, and an ambient pressure feedback component 516. The operations and functionalities of these components are described below.

The calibration-compensation-conversion component 502 can be coupled to a flow sensor (e.g., the flow sensor 402) and can receive one or more signals from the flow sensor as described above. The calibration-compensation-conversion component 502 can also receive one or more signals relating to calibration, conversion, or compensation parameters. The calibration-compensation-conversion component 502 can operate to determine and output fluid path flow (e.g., µL/min) based on the signals from the flow sensor. Accordingly, the calibration-compensation-conversion component 502 can output a fluid path flow signal indicating instantaneous flow rate. The calibration, conversion, or compensation parameters can also operate to provide sensor calibration and/or compensation functions such as, for example, linearization of output, input/output offset correction, and/or temperature compensation.

The delivery error estimation component 504 can receive the fluid path instantaneous flow rate output signal from the calibration-compensation-conversion component 502. The delivery error estimation component 504 can also receive fluid capacitance values (e.g., system calibration values), ambient pressure baseline values, and a clock signal (e.g., from an external clock) as shown in FIG. 5. The delivery error estimation component 504 can operate to determine instantaneous volumetric delivery error (e.g., an amount of over-delivery or under-delivery) and can output a signal indicating the same. To determine the instantaneous volumetric delivery error, the delivery error estimation component 504 can integrate indicators of fluid path flow to determine instantaneous volumetric flow error. The delivery error estimation component 504 can also compensate for ambient pressure changes which could cause unintended flow to occur.

The delivery error tracking and alarm determination component 506 can receive the instantaneous volumetric delivery error signal outputted by the delivery error estimation component 504. The delivery error tracking and alarm determination component 506 can also receive time-based de-rating factors, an ambient pressure model error, and an indication of intended volumetric delivery as shown in FIG. 5. Based on these input signals, the delivery error tracking and alarm determination component 506 can generate an alert or alarm signal as necessary as described above. The delivery error tracking and alarm determination component 506 can compare the intended volumetric delivery against the sum of ambient pressure model error and instantaneous volumetric delivery error as modified by time based de-rating factors. Threshold comparisons can also be made to determine if an alarm signal should be generated. If an alarm condition is determined, a signal indicating the same can be generated and outputted.

The ambient pressure model 508 can receive an ambient pressure signal from the ambient pressure feedback component 516. The ambient pressure model 508 can output an ambient pressure model error. The ambient pressure model 508 can track background ambient pressure changes to limit false alarms due to ambient pressure or back pressure changes. The ambient pressure model 508 can also track background ambient pressure changes to determine over-delivery and/or under-delivery due to significant pressure excursions.

The intended delivery model component 510 can receive pump control data (e.g., a count of the number of pulses delivered) and can receive pump characteristic performance data (e.g., a measure of volume per pulse delivery). The intended delivery model component 510 can generate an indication of expected volumetric delivery as shown in FIG. 5. The intended delivery model component 510 can track the expected delivery as commanded by the pump system for comparison in the delivery error tracking and alert-alarm determination component 506.

The time-based decay alert-alarm parameter storage 512 can receive and/or store system alert-alarm decay parameters. The time-based decay alert-alarm parameter storage 512 can output specific mathematical functions to de-rate the impact of instantaneous volumetric error over time. The time-based decay alert-alarm parameter storage 512 can ensure transient unintended delivery events do not accumulate in the system and lead to unnecessary alarms.

The alert-alarm actuator 514 can receive any alert-alarm signal from the Delivery error tracking and alarm determination component 506. Based upon receipt of any alert-alarm signal, the Alert-alarm actuator 514 can activate an alarm mechanism as described above including, for example, a visual and/or audible alarm to notify the user of an urgent condition.

The ambient pressure feedback component 516 can provide ambient pressure feedback (e.g., in psi) via an absolute pressure sensor (e.g., not sensing the fluid path). This ambient pressure feedback component 516 can be optional to help account for events in between flow sampling.

Figure 6:
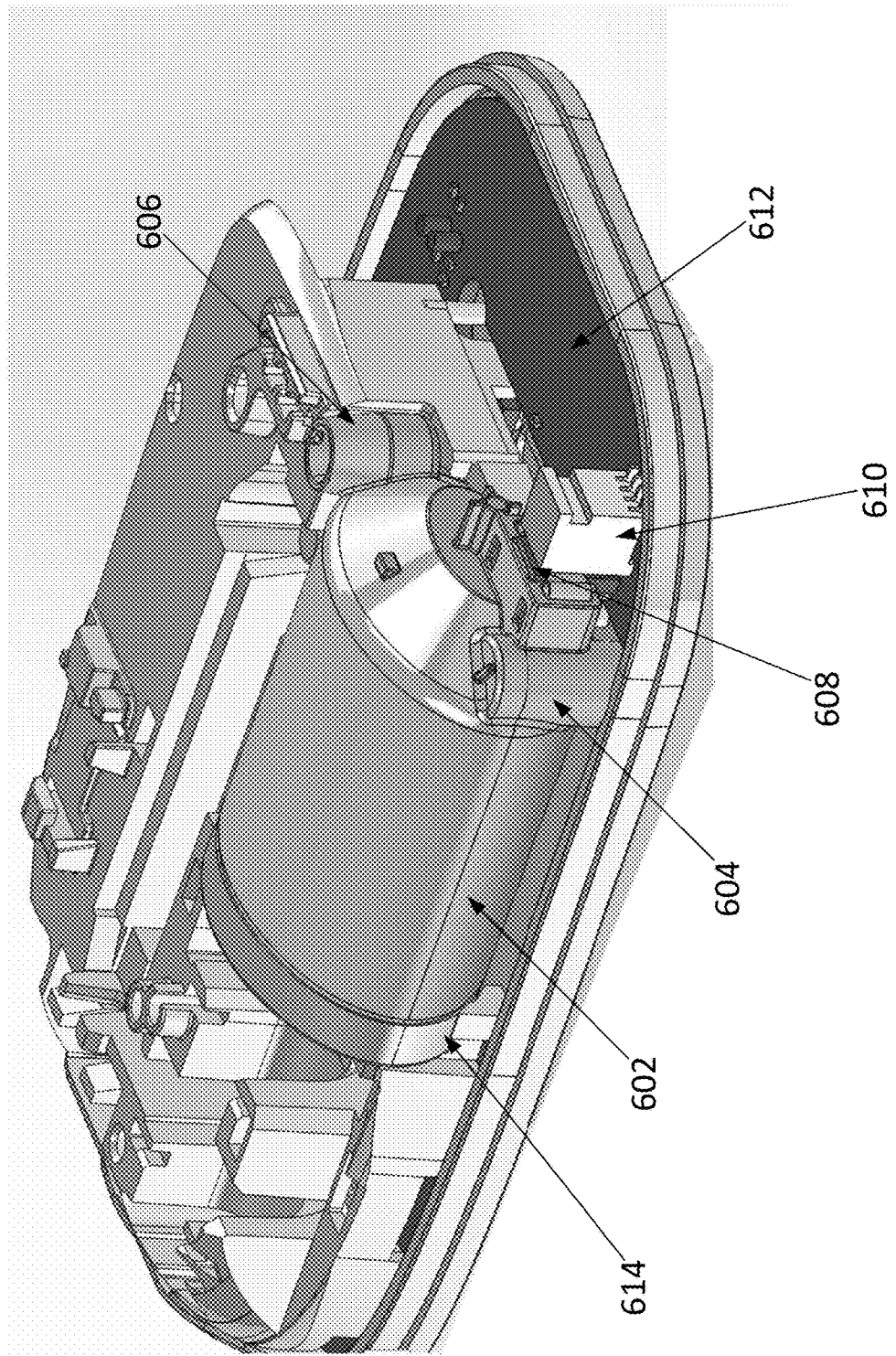
FIG. 6 illustrates an exemplary drug delivery device.

FIG. 6 illustrates an exemplary drug delivery device 600. The drug delivery device 600 can represent any of the drug delivery devices described herein. The drug delivery device 600 can be a wearable drug delivery device. The drug delivery device 600 can be designed to deliver any type of drug, medicine, therapeutic agent, or infusate to a user such as, for example, insulin. The drug delivery device 600 can be a single-use device (e.g., filled once and used once and then discarded) or can be a multiple-use device (e.g., filled one or more times and used after one or more fillings).

In various embodiments, the drug delivery device 100 can be provided to a user without any included drug or medicine. Under such a scenario, a user may, for example, fill a reservoir of the drug delivery device 600 with a medicine or drug (e.g., by transferring a fluid from a syringe to a reservoir of the drug delivery device 600).

The drug delivery device 600 can be an infusion device, including a drug delivery pump device as described herein. The drug delivery device 600 may provide a stored drug to a user over a relatively long period of time (e.g., over several days in small dosage amounts) or over a relatively short period of time (e.g., over a few hours to a day). In various embodiments, the drug delivery device 600 can be an OmniPod® (Insulet Corporation, Billerica, Mass.) insulin delivery device. The drug delivery device 600 can be a drug delivery device such as those described in U.S. Pat. No. 7,303,549, 7,137,964, or 6,740,059, each of which is incorporated herein by reference in its entirety.

In various embodiments, the drug delivery device can include the pump systems described herein including the pump system 200 or the pump system 400 as well as the corresponding implementations of the monitoring component 204 described in relation to FIGS. 3 and 5, respectively. Overall, the drug delivery device 100 can include the monitoring of over-delivery and under-delivery of an infusate to a patient during intended delivery periods and intended non-delivery periods according to the techniques described herein.

Various internal constituent components of the drug delivery device 600 are shown in FIG. 6. A top or cover of the drug delivery device 600 is not shown so as to provide a view of the various internal components and features of the drug delivery device 600. As shown in FIG. 6, the drug delivery device 600 can include a reservoir or pump reservoir 602, a reservoir inlet 604, a reservoir outlet 606, a sensor 608, a sensor assembly 610, a printed circuit board assembly (PCBA) 612, and structural support component 614.

The pump reservoir 602 can hold or store the drug or medicine that can be delivered to a user (e.g., insulin). The pump reservoir 602 can be accessed or filled through the reservoir inlet 604. The reservoir inlet 604 can provide a path for transferring a fluid from outside of the drug delivery device 600 to inside the drug delivery device 600 for storage and subsequent delivery. The drug stored in the pump reservoir 602 can exit the pump reservoir 602 through the reservoir outlet 606 for delivery to the user. The drug delivery device 600 can include a pump for transferring the drug from the reservoir 602 to a user. In various embodiments, a plunger acting in conjunction with the reservoir 602 can operate as a pump to enable the stored fluid to be expelled for delivery to a patient through a fluid path (e.g., as described in relation to the pumps systems 200 and 400). When extracted by operation of the pump, the drug may follow a path from the reservoir 602 to an outlet of the drug delivery device 602 and the on to a patient.

The sensor 608 can be a pressure sensor (e.g., the pressure sensor 202) and can operate and provide the functionality described above. The sensor 608 can be incorporated into the fluid path of the drug delivery device 600 (e.g., incorporated into the reservoir 602). The sensor 608 can be coupled to a sensor assembly or sensor interface 610. The sensor assembly 610 can provide connectivity between the sensor 608 and the PCBA 612. The PCBA 612 can house or contain additional functional components for operating the drug delivery device 600 including, for example, a controller for operating the drug pump to deliver stored fluid from the reservoir 602 to the user. The PCBA 612 can further house or contain components related to user interaction or control components as well as user feedback components including, such as, any of the alarm mechanisms or components described herein. Signals can be transferred bidirectionally between the sensor 608 and the PCBA 612 (and any other components coupled to the PCBA 612) by way of the interface 610. The monitoring component 204 can be integrated across any number of components included in the drug delivery device 600 and can, in various embodiments, include a processor and associated memory, dedicated hardware, or any device capable of executing instructions (e.g., computer executable code, firmware, etc.).

The structural support component 614 can correspond to the structural support component 108 represented in FIGS. 1, 2, and 4. The structural support component 614 can provide mechanical structural support for the reservoir 602 as well as the plunger and fluid path of the drug delivery device 600 and so can include any component of the drug delivery device 600 that supports these components.

Figure 11:
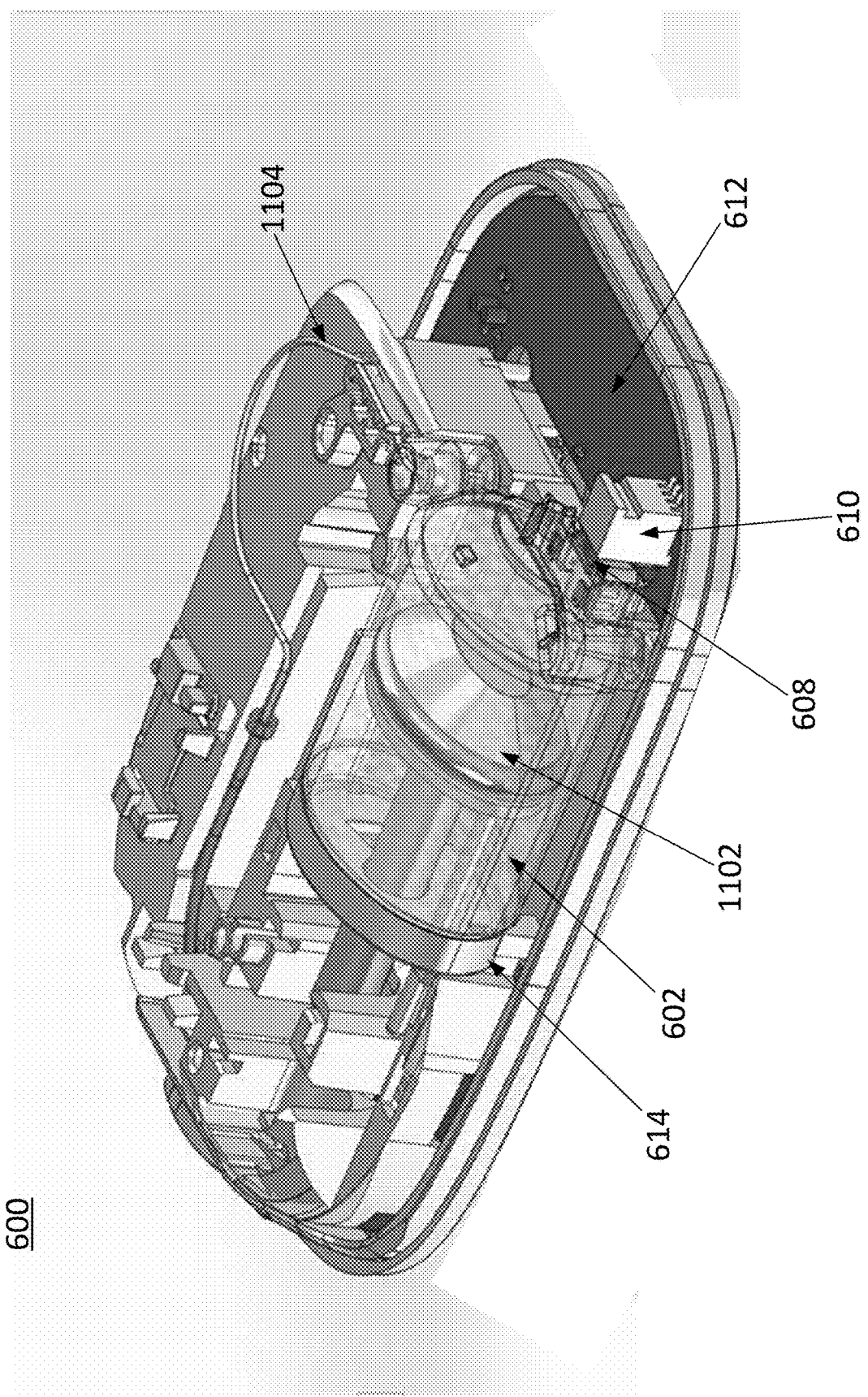
FIG. 11 illustrates a second view of the exemplary drug delivery device of FIG. 6.

FIG. 11 illustrates the drug delivery device 600 depicted in FIG. 6 with a transparent version of the reservoir 602 to reveal additional detail of the drug delivery device 600. As shown in FIG. 11, the drug delivery device 600 includes a plunger 1102 that can be positioned within the reservoir 602. An end portion or stem of the plunger 1102 can extend outside of the reservoir 602. The plunger 1102 can expel the liquid drug from the reservoir 602 by advancing into the reservoir 602. The plunger 1102 can be advanced by a plunger or pump drive mechanism that can be coupled to the plunger 1102 as described above (not illustrated in FIG. 11 for simplicity).

FIG. 11 further illustrates a fluid path component 1104. The fluid path component 1104 can couple the reservoir 602 to a user of the drug delivery device 600. The liquid drug expelled from the reservoir 602 can be provided to the patient by way of the fluid path component 1104. The fluid path component 1104 can correspond to the representation of the fluid path component 106 depicted in FIGS. 1, 2, and 4.

FIGS. 7-10 illustrates various techniques for incorporating a pressure sensor (e.g., the pressure sensor 202) into the fluid path of a pump system—in particular, a pump system included within the drug delivery device 600.

Figure 7:
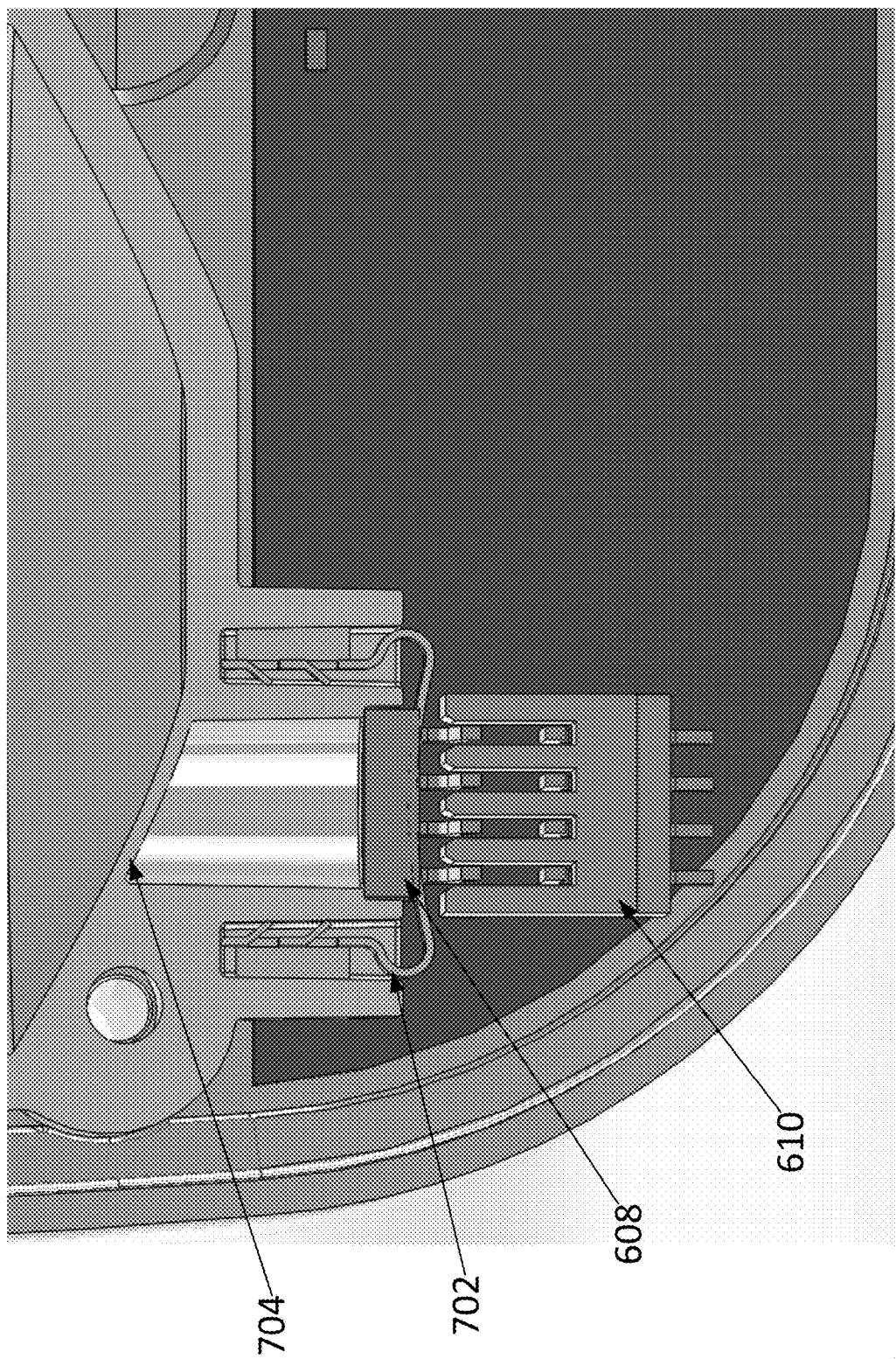
FIG. 7 illustrates a first exemplary incorporation of a pressure sensor into the drug delivery device of FIG. 6.

FIG. 7 illustrates a sensor retention clip 702 coupled to the sensor 608 and a pressure transfer membrane 704. The pressure transfer membrane 704 can isolate the sensor 608 from the fluid path—for example, a liquid drug stored in the reservoir 602. The pressure transfer membrane 704 can react to a displacement force caused by, for example, a pumping action to expel a liquid drug from the reservoir 602. The sensor retention clip 702 can help maintain a positioning of the sensor 608 as it responds to (e.g., and monitors and/or measures) changes in pressure that may be caused by any displacement force. A force transfer potting (not shown in FIG. 7 for simplicity) can be used to transfer changes in pressure for measurement by the sensor 608 and can be positioned between the sensor 608 and the membrane 704.

Figure 8:
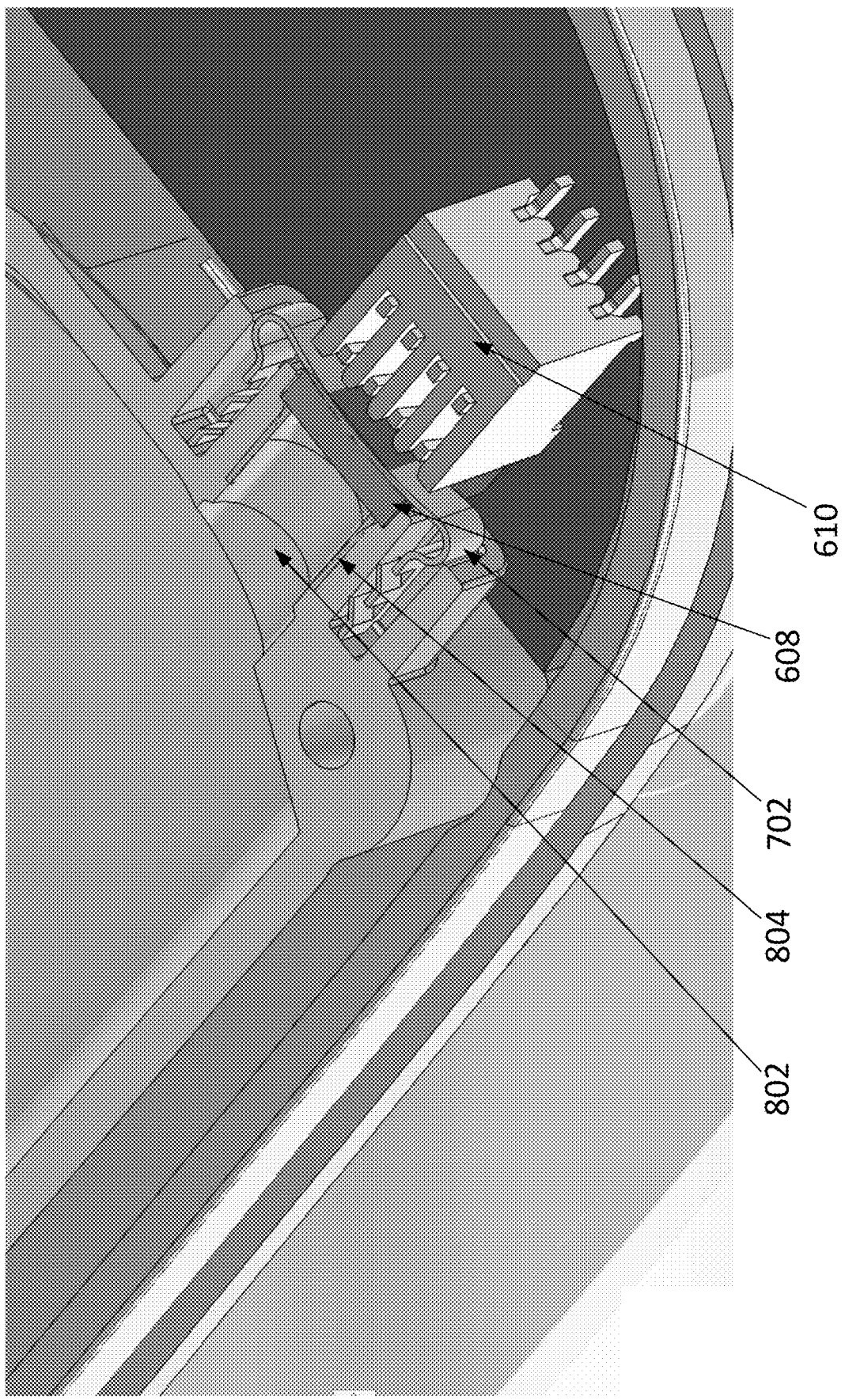
FIG. 8 illustrates a second exemplary incorporation of a pressure sensor into the drug delivery device of FIG. 6.

FIG. 8 illustrates the sensor 608 positioned within a pressure sensor installation port 802. The sensor 608, as described above, can have a round shape and can be fitted into the installation port 802 to form a tight fit with the reservoir 602. The sensor 608 can include a portion 804 that extends into the installation port 802. The sensor 608 and portion 804 can be isolated from the fluid path of the drug delivery device 600 by the walls of the reservoir 602 and the sensor 608 and extended portion 804. The sensor 608 and the extended portion 804 can be pressed into an undersized bore forming a portion of the installation port 802 to ensure an air-tight and liquid-tight seal (e.g., a hermetic seal). The engagement of the sensor 608 with the fluid path as shown in FIG. 8 can be considered to be a long engagement press fit. The arrangement shown in FIG. 8 can further include force transfer potting (not shown in FIG. 8 for simplicity) as will be understood by a person of ordinary skill in the art.

Figure 9:
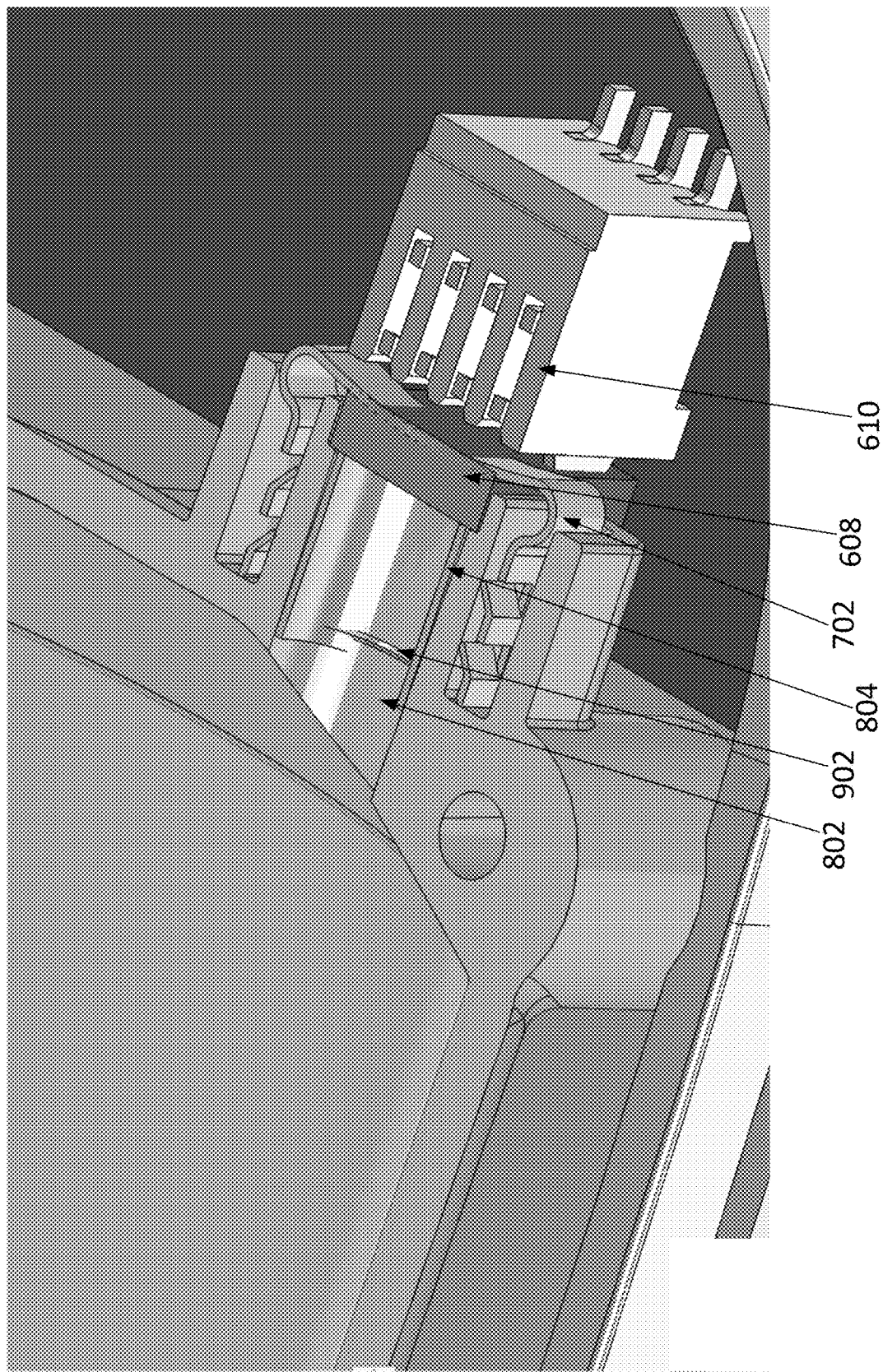
FIG. 9 illustrates a third exemplary incorporation of a pressure sensor into the drug delivery device of FIG. 6.

FIG. 9 illustrates the sensor 608 positioned within the pressure sensor installation port 802 and an integral radial point seal 902 positioned with the installation port 802. The radial seal 902 can be positioned anywhere along the extended portion 804 and can be molded into the walls of the reservoir 602/installation port 802. The radial seal 902 can further help isolate the sensor 608 from the fluid path of the drug delivery device 600. The arrangement shown in FIG. 9 can further include force transfer potting (not shown in FIG. 9 for simplicity) as will be understood by a person of ordinary skill in the art.

Figure 10:
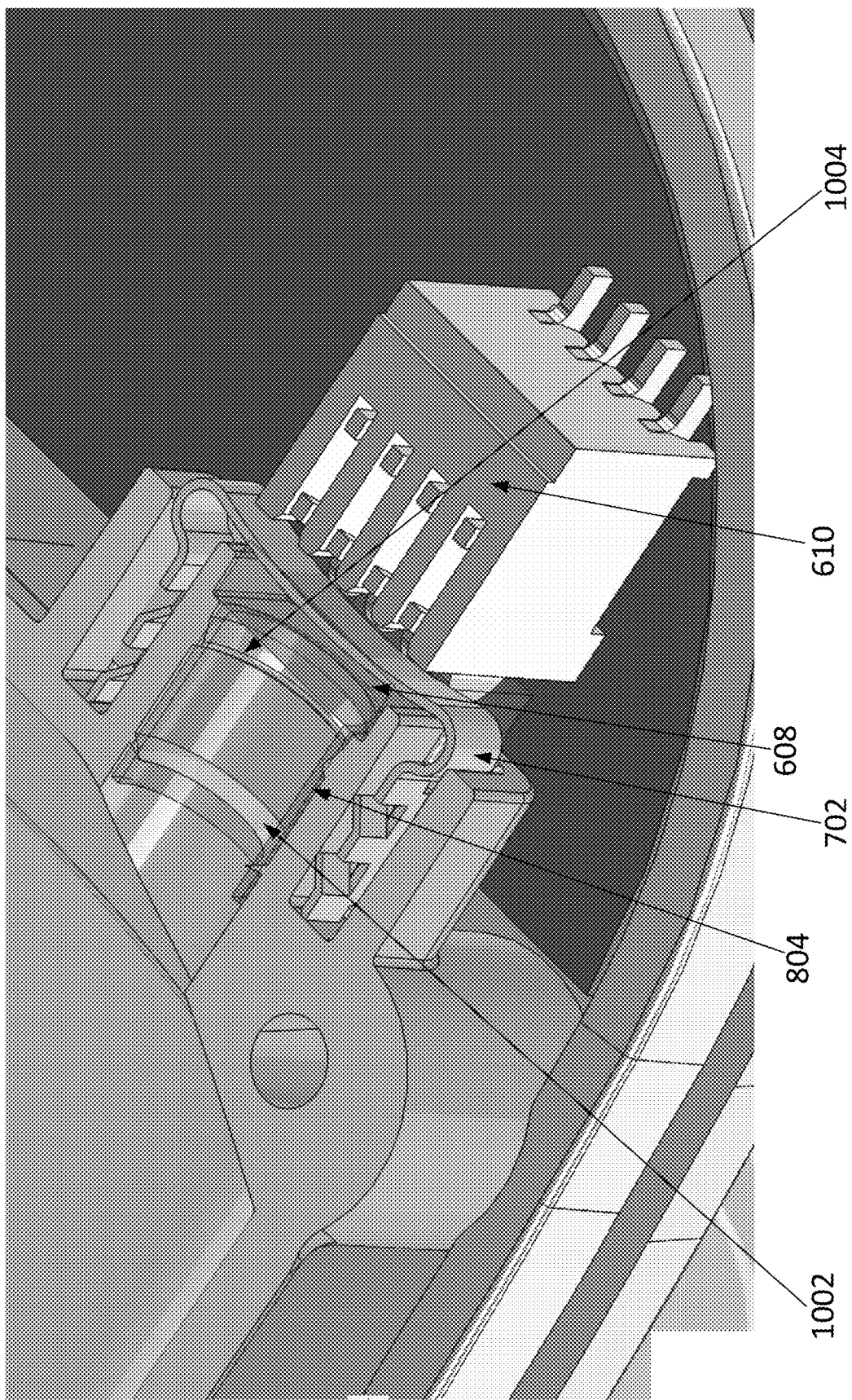
FIG. 10 illustrates a fourth exemplary incorporation of a pressure sensor into the drug delivery device of FIG. 6.

FIG. 10 illustrates the sensor 608 positioned within the pressure sensor installation port 802 and a radial lip seal 1002 and a radial point seal 1004. The radial lip seal 1002 and the radial point seal 1004 can be molded into the walls of the reservoir 602/installation port 802. The sensor 608 and extended portion 804 thereof can be pressed into the installation port 802 and can engage the radial lip seal 1002 and the radial point seal 1004. The radial lip seal 1002 radially extends into an open area of the installation port 802. The radial lip seal 1002 can form a pointed end feature that can bend out of the way when the sensor 608 and extended portion 804 are pressed into the installation port 802. The radial lip seal 1002 provides a further isolating sealing feature. Pressure can cause the seal between the sensor 608, the extended portion 804, and/or the walls of the reservoir 602 to engage the radial lip seal 1002 in a tighter manner, thereby resulting in a better or tighter seal as pressure increases (e.g., as more of the liquid drug is expelled from the reservoir 602). The arrangement shown in FIG. 10 can further include force transfer potting (not shown in FIG. 10 for simplicity) as will be understood by a person of ordinary skill in the art.

In various embodiments, during an operation to provide a drug to a user, when a pump pulse occurs, a sharp rise in pressure can be sensed, followed by a slow decay as the pulse exits a narrow pump cannula of a drug delivery device. By monitoring the pressure spike and the corresponding decay, any of the pump systems (e.g., pump systems 200 or 400) or drug delivery devices described herein can determine if fluid is flowing, or if there is in an occlusion.

Pressure spikes that may occur when a pulse is not being delivered can be due to external effects (e.g., flying, swimming, physiological changes). By comparing pressure changes to the characteristic fluid capacitance, techniques described herein can determine if unexpected under-delivery or over-delivery of the drug has occurred in real time. Further, by comparing delivery conditions to a baseline and non-delivery conditions to the baseline, under-delivery and over-delivery conditions may be detected, as described herein.

The pump systems (e.g., pump systems 200 or 400) or drug delivery devices described herein, including techniques described herein performed by these devices, can provide numerous benefits over conventional drug delivery devices. In particular, the techniques described herein can provide virtual real-time occlusion detection. Further, the techniques can distinguish an occlusion (e.g., a no flow or low flow condition) from an increase in back pressure (e.g., increased resistance with continual flow). Additionally, the techniques described herein can track and log data (e.g., pressure change information) related to excursions from stated altitude or depth specifications.

The following examples pertain to additional further embodiments:

Example 1 is a method comprising determining a first pressure at a start of a delivery operation for a liquid drug, determining a second pressure at an end of the delivery operation for the liquid drug, determining a fluid capacitance value of a fluid path used for the delivery operation of the liquid drug, and determining an intended liquid drug delivery amount, and determining a delivery error amount of the liquid drug based on the first and second pressures, the fluid capacitance value, and the intended liquid drug delivery amount.

Example 2 is an extension of Example 1 or any other example disclosed herein, further comprising determining the first and second pressures based on determining an absolute pressure.

Example 3 is an extension of Example 2 or any other example disclosed herein, further comprising comparing the delivery error amount to one or more thresholds.

Example 4 is an extension of Example 3 or any other example disclosed herein, further comprising determining an over-delivery condition when the delivery error amount is greater than a first threshold.

Example 5 is an extension of Example 4 or any other example disclosed herein, further comprising determining an under-delivery condition when the delivery error amount is less than a second threshold.

Example 6 is an extension of Example 5 or any other example disclosed herein, further comprising providing a first alarm in response to the over-delivery condition and providing a second, different alarm in response to the under-delivery condition.

Example 7 is an extension of Example 6 or any other example disclosed herein, wherein the first and second alarms comprise at least one of an audible, a visual, and a tactile indication.

Example 8 is an extension of Example 7 or any other example disclosed herein, further comprising adjusting an indication of urgency of at least one of the first and second alarms based on a determined severity of the over-delivery condition and the under-delivery condition, respectively.

Example 9 is an extension of Example 6 or any other example disclosed herein, further comprising dynamically adjusting the first and second thresholds.

Example 10 is an extension of Example 9 or any other example disclosed herein, further comprising dynamically adjusting the first and second thresholds based on a de-rating factor based on a determined total amount of delivered liquid drug.

Example 11 is an extension of Example 9 or any other example disclosed herein, further comprising dynamically adjusting the first and second thresholds based on a de-rating factor based on a determined unmetabolized excess amount of over-delivered liquid drug.

Example 12 is an extension of Example 9 or any other example disclosed herein, further comprising determining a rate of change of atmospheric pressure.

Example 13 is an extension of Example 12 or any other example disclosed herein, further comprising dynamically adjusting the first and second thresholds based on the determined rate of change of the atmospheric pressure.

Example 14 is an extension of Example 9 or any other example disclosed herein, further comprising determining a temperature.

Example 15 is an extension of Example 14 or any other example disclosed herein, further comprising dynamically adjusting the first and second thresholds based on the determined temperature.

Example 16 is an extension of Example 1 or any other example disclosed herein, further comprising determining an unintended delivery error amount of the liquid drug during a time outside of the delivery operation of the liquid drug.

Example 17 is an extension of Example 16 or any other example disclosed herein, further comprising comparing the unintended delivery error amount to one or more unintended delivery thresholds.

Example 18 is an extension of Example 17 or any other example disclosed herein, further comprising providing an alarm responsive to comparing the unintended delivery error amount to the one or more unintended delivery thresholds.

Example 19 is an apparatus comprising a reservoir configured to hold a liquid drug, a fluid path component configured to couple the reservoir to a user, a plunger configured to expel the liquid drug from the reservoir for delivery to the user, an absolute pressure sensor configured to detect atmospheric pressure and relative pressure, and a monitoring component configured to determine a delivery error amount during an intended delivery operation and an unintended delivery operation based on the atmospheric pressure and the relative pressure.

Example 20 is an extension of Example 19 or any other example disclosed herein, wherein the plunger is directed to expel the liquid drug from the reservoir during an intended delivery operation and is directed to not expel the liquid drug from the reservoir during an unintended delivery operation.

Example 21 is an extension of Example 20 or any other example disclosed herein, wherein the monitoring component indicates an over-delivery condition when the delivery error amount is greater than a first threshold and wherein the monitoring component indicates an under-delivery condition when the delivery error amount is less than a second, different threshold.

Example 22 is an extension of Example 21 or any other example disclosed herein, wherein the monitoring component is configured to generate an alarm signal based on a determined severity of at least one of the over-delivery condition and the under-delivery condition.

Example 23 is an extension of Example 22 or any other example disclosed herein, wherein the alarm signal comprises at least one of a visual, an audible, and a tactile alert.

Example 24 is an extension of Example 21 or any other example disclosed herein, wherein the monitoring component is configured to dynamically adjust the first and second thresholds.

Example 25 is an extension of Example 24 or any other example disclosed herein, further comprising a temperature sensor, the monitoring component configured to dynamically adjust the first and second thresholds based on at least one of a determined temperature and a de-rating factor based on a determined total amount of delivered liquid drug.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method for controlling a pump system, the pump system having a housing and a monitoring component including circuitry, the method comprising:
   receiving by the monitoring component a first signal from a pressure sensor indicative of a first pressure at a start of a delivery operation for a liquid drug;
   determining by the monitoring component the first pressure at the start of the delivery operation for the liquid drug based on the received first signal;
   receiving a second signal from the pressure sensor indicative of a second pressure at an end of the delivery operation for the liquid;
   determining, by the monitoring component the second pressure at the end of the delivery operation for the liquid drug based on the received second signal;
   determining, by the monitoring component a fluid capacitance value of a fluid path used for the delivery operation of the liquid drug;
   determining an intended liquid drug delivery amount;
   determining a delivery error amount of the liquid drug based on the first and second pressures, the fluid capacitance value, and the intended liquid drug delivery amount; and
   in response to the determined delivery error amount, the monitoring component actuates an alarm actuator by outputting an alert-alarm signal to the alarm actuator, the alarm actuator configured to actuate an alarm.

2. The method of claim 1, further comprising determining the first and second pressures based on determining an absolute pressure.

3. The method of claim 2, further comprising comparing the delivery error amount to one or more thresholds.

4. The method of claim 3, further comprising determining an over-delivery condition when the delivery error amount is greater than a first threshold.

5. The method of claim 4, further comprising determining an under-delivery condition when the delivery error amount is less than a second threshold.

6. The method of claim 5, wherein the alarm includes a first alarm in response to the over-delivery condition, and a second alarm in response to the under-delivery condition, wherein the first and second alarms are different.

7. The method of claim 6, wherein the first and second alarms comprise at least one of an audible, a visual, and a tactile indication.

8. The method of claim 7, further comprising adjusting an indication of urgency of at least one of the first and second alarms based on a determined severity of the over-delivery condition and the under-delivery condition, respectively.

9. The method of claim 6, further comprising dynamically adjusting the first and second thresholds.

10. The method of claim 9, further comprising dynamically adjusting the first and second thresholds based on a de-rating factor based on a determined total amount of delivered liquid drug.

11. The method of claim 9, further comprising dynamically adjusting the first and second thresholds based on a de-rating factor based on a determined unmetabolized excess amount of over-delivered liquid drug.

12. The method of claim 9, further comprising determining a rate of change of atmospheric pressure.

13. The method of claim 12, further comprising dynamically adjusting the first and second thresholds based on the determined rate of change of the atmospheric pressure.

14. The method of claim 5, further comprising:
determining a temperature; and
dynamically adjusting the first and second thresholds based on the determined temperature.

15. The method of claim 1, further comprising determining an unintended delivery error amount of the liquid drug during a time outside of the delivery operation of the liquid drug.

16. The method of claim 15, further comprising:
comparing the unintended delivery error amount to one or more unintended delivery thresholds,
wherein the alarm is responsive to the comparison of the unintended delivery error amount to the one or more unintended delivery thresholds.

17. An apparatus, comprising:
a reservoir configured to hold a liquid drug;
a fluid path component configured to couple the reservoir to a user;
a plunger configured to expel the liquid drug from the reservoir for delivery to the user; an absolute pressure sensor configured to detect atmospheric pressure and relative pressure; and
a monitoring component including circuitry configured to:
receive a first signal from a pressure sensor indicative of a first pressure at a start of a delivery operation for a liquid;
determine the first pressure at the start of the delivery operation for the liquid drug based on the received first signal;
receive a second signal from the pressure sensor indicative of a second pressure at an end of the delivery operation for the liquid;
determine the second pressure at the end of the delivery operation for the liquid drug based on the second signal;
determine a fluid capacitance value of a fluid path used for the delivery operation of the liquid drug;
determine an intended liquid drug delivery amount;
determine a delivery error amount of the liquid drug based on the first and second pressures, the fluid capacitance value, and the intended liquid drug delivery amount; and
in response to the determined delivery error amount, actuate an alarm actuator by outputting an alert-alarm signal, the alarm actuator configured to activate an alarm.

18. The apparatus of claim 17, wherein the plunger is directed to expel the liquid drug from the reservoir during an intended delivery operation and is directed to not expel the liquid drug from the reservoir during an unintended delivery operation.

19. The apparatus of claim 18, wherein the monitoring component indicates an over-delivery condition when the delivery error amount is greater than a first threshold and wherein the monitoring component indicates an under-delivery condition when the delivery error amount is less than a second, different threshold.

20. The apparatus of claim 19, wherein the monitoring component is configured to generate the alert-alarm signal based on a determined severity of at least one of the over-delivery condition and the under-delivery condition.

21. The apparatus of claim 20, wherein the alarm comprises at least one of a visual, an audible, and a tactile alert.

22. The apparatus of claim 19, wherein the monitoring component is configured to dynamically adjust the first and second thresholds.

23. The apparatus of claim 22, further comprising a temperature sensor, the monitoring component configured to dynamically adjust the first and second thresholds based on at least one of a determined temperature and a de-rating factor based on a determined total amount of delivered liquid drug.

24. The method of claim 1, wherein the first signal is received at first point in time and the second signal is received at a point in time later than when the first signal is received.

25. The method of claim 1, wherein the fluid capacitance changes in response to effective stiffness of a reservoir containing the liquid drug as a plunger is advanced further into the reservoir by a plunger drive mechanism coupled to the monitoring component.

* * * * *